(12) United States Patent  (10) Patent No.: US 8,206,636 B2
Ramzipoor et al.  (45) Date of Patent: *Jun. 26, 2012

(54) STENT FABRICATION VIA TUBULAR CASTING PROCESSES

(75) Inventors: Kamal Ramzipoor, Fremont, CA (US); Alfred N. K. Chia, Singapore (SG); Liwei Wang, Singapore (SG); Chang Y. Lee, Redwood City, CA (US)

(73) Assignee: Amaranth Medical Pte., Singapore (SG)

( * ) Notice: Subject to any disclaimer, the term of this patent is extended or adjusted under 35 U.S.C. 154(b) by 209 days.

This patent is subject to a terminal disclaimer.

(21) Appl. No.: 12/488,453

(22) Filed: Jun. 19, 2009

(65) Prior Publication Data

US 2010/0004734 A1  Jan. 7, 2010

Related U.S. Application Data

(63) Continuation-in-part of application No. 12/143,659, filed on Jun. 20, 2008.

(51) Int. Cl.
*B28B 5/02* (2006.01)
*B29C 43/22* (2006.01)
*B29D 22/00* (2006.01)
*A61K 49/04* (2006.01)
*A61K 31/727* (2006.01)
*A61F 2/00* (2006.01)

(52) U.S. Cl. ........ 264/294; 264/503; 264/573; 424/426; 424/9.41; 514/56

(58) Field of Classification Search .................. 264/294, 264/503, 573; 424/426, 9.41; 514/56
See application file for complete search history.

(56) References Cited

U.S. PATENT DOCUMENTS

| 4,173,689 A | 11/1979 | Lyman et al. |
| 4,334,327 A | 6/1982 | Lyman et al. |
| 4,661,530 A | 4/1987 | Gogolewski et al. |
| 4,770,664 A | 9/1988 | Gogolewski |
| 4,834,747 A | 5/1989 | Gogolewski |
| 4,955,899 A | 9/1990 | Della Corna et al. |
| 5,104,400 A | 4/1992 | Berguer et al. |
| 5,152,782 A | 10/1992 | Kowligi et al. |
| 5,670,161 A | 9/1997 | Healy et al. |
| 5,935,164 A | 8/1999 | Iversen |
| 5,935,506 A | 8/1999 | Schmitz et al. |
| 6,090,134 A | 7/2000 | Tu et al. |
| 6,153,252 A | 11/2000 | Hossainy et al. |

(Continued)

FOREIGN PATENT DOCUMENTS

WO   WO 2009/155560   12/2009

*Primary Examiner* — Christina Johnson
*Assistant Examiner* — Michael Piery
(74) *Attorney, Agent, or Firm* — Levine Bagade Han LLP

(57) ABSTRACT

Tubular casting processes, such as dip-coating, may be used to form substrates from polymeric solutions which may be used to fabricate implantable devices such as stents. The polymeric substrates may have multiple layers which retain the inherent properties of their starting materials and which are sufficiently ductile to prevent brittle fracture. Parameters such as the number of times the mandrel is immersed, the duration of time of each immersion within the solution, as well as the delay time between each immersion or the drying or curing time between dips and withdrawal rates of the mandrel from the solution may each be controlled to result in the desired mechanical characteristics. Additional post-processing may also be utilized to further increase strength of the substrate or to alter its shape.

37 Claims, 16 Drawing Sheets

U.S. PATENT DOCUMENTS

| | | |
|---|---|---|
| 6,217,815 B1 | 4/2001 | Sisbarro |
| 6,231,326 B1 | 5/2001 | Sisbarro |
| 6,322,847 B1 | 11/2001 | Zhong et al. |
| 6,635,082 B1 | 10/2003 | Hossainy et al. |
| 6,833,153 B1 | 12/2004 | Roorda et al. |
| 6,860,946 B2 | 3/2005 | Hossainy et al. |
| 6,866,805 B2 | 3/2005 | Hong et al. |
| 6,989,071 B2 | 1/2006 | Kocur et al. |
| 7,112,298 B2 | 9/2006 | Kampa et al. |
| 7,311,727 B2 | 12/2007 | Mazumder et al. |
| 2003/0050687 A1 | 3/2003 | Schwade et al. |
| 2003/0060836 A1 | 3/2003 | Wang et al. |
| 2003/0157241 A1 | 8/2003 | Hossainy et al. |
| 2003/0195628 A1* | 10/2003 | Bao et al. .................. 623/17.12 |
| 2003/0225447 A1 | 12/2003 | Majercak et al. |
| 2004/0030377 A1 | 2/2004 | Dubson et al. |
| 2004/0113306 A1 | 6/2004 | Rapacki et al. |
| 2004/0127932 A1 | 7/2004 | Shah |
| 2004/0127970 A1 | 7/2004 | Saunders et al. |
| 2004/0164030 A1 | 8/2004 | Lowe et al. |
| 2005/0187608 A1 | 8/2005 | O'Hara |
| 2006/0025852 A1 | 2/2006 | Armstrong et al. |
| 2006/0122686 A1 | 6/2006 | Gilad et al. |
| 2006/0142736 A1 | 6/2006 | Hissink et al. |
| 2006/0149365 A1 | 7/2006 | Fifer et al. |
| 2006/0212064 A1 | 9/2006 | Shah |
| 2006/0259133 A1 | 11/2006 | Sowinski et al. |
| 2006/0287715 A1 | 12/2006 | Atladottir et al. |
| 2007/0038290 A1 | 2/2007 | Huang et al. |
| 2007/0100430 A1 | 5/2007 | Rudakov et al. |
| 2007/0106361 A1 | 5/2007 | Epstein |
| 2007/0110889 A1 | 5/2007 | Sundar |
| 2007/0185561 A1 | 8/2007 | Schmitz et al. |
| 2007/0202046 A1* | 8/2007 | Dave .......................... 424/9.41 |
| 2007/0250153 A1 | 10/2007 | Cully et al. |
| 2007/0281117 A1 | 12/2007 | Kaplan et al. |
| 2007/0283552 A1 | 12/2007 | Gale et al. |
| 2008/0051866 A1 | 2/2008 | Chen et al. |
| 2008/0091275 A1 | 4/2008 | Ducharme |
| 2008/0103584 A1 | 5/2008 | Su et al. |
| 2009/0319028 A1* | 12/2009 | Ramzipoor et al. ......... 623/1.17 |

* cited by examiner

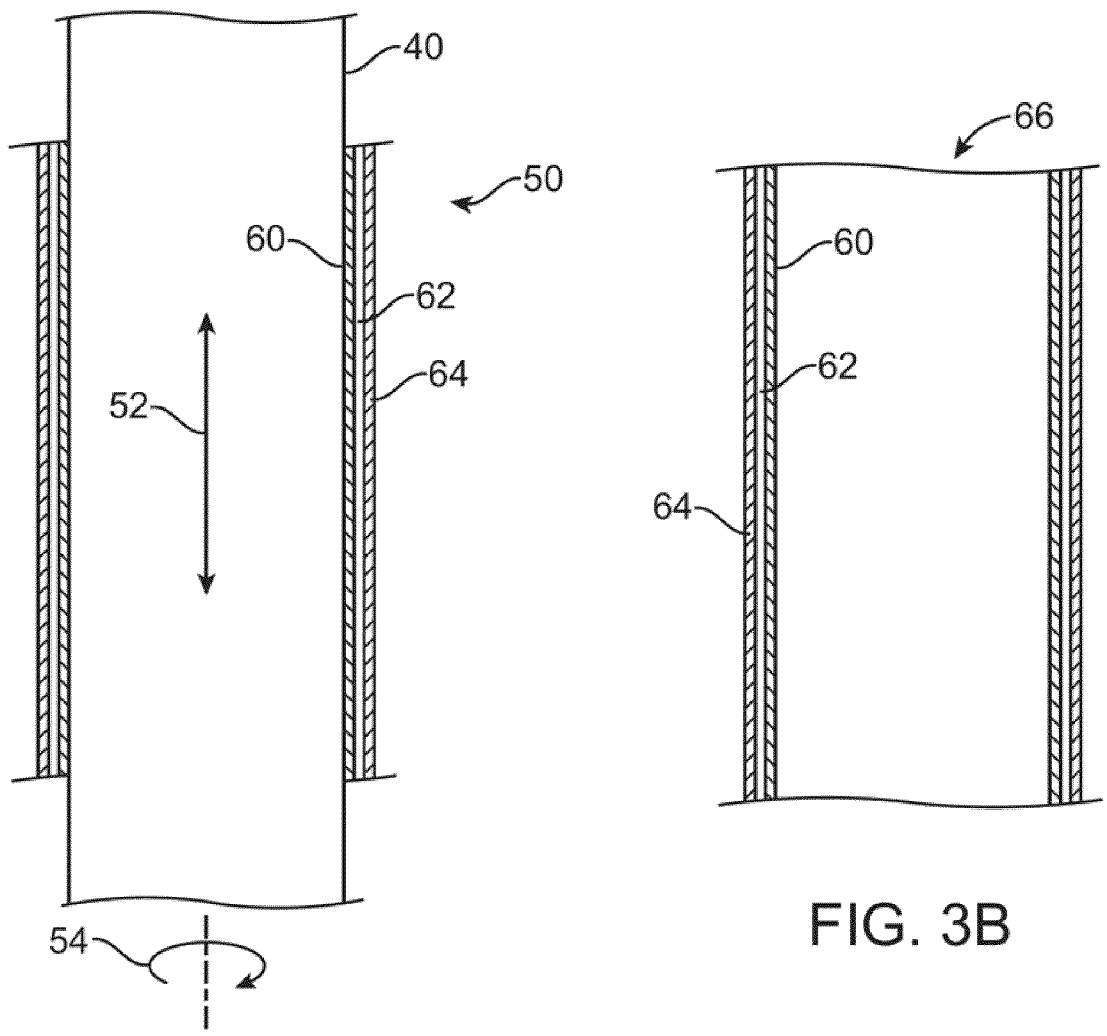
FIG. 3B
FIG. 3A
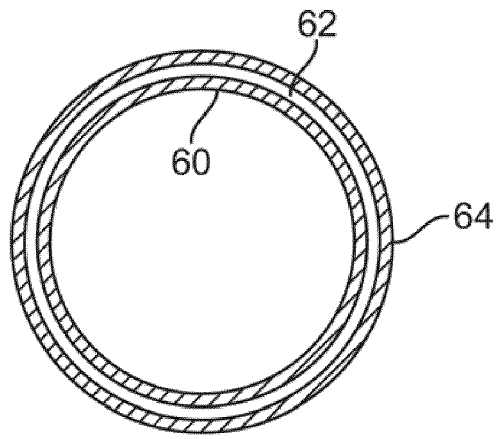
FIG. 3C

STENT FABRICATION VIA TUBULAR CASTING PROCESSES

CROSS-REFERENCE TO RELATED APPLICATIONS

This application is a continuation-in-part of U.S. patent application Ser. No. 12/143,659 filed Jun. 20, 2008, which is incorporated herein by reference in its entirety.

FIELD OF THE INVENTION

The present invention relates generally to manufacturing processes for forming or creating devices which are implantable within a patient, such as medical devices. More particularly, the present invention relates to methods and processes for forming or creating tubular substrates which may be further processed to create medical devices having various geometries suitable for implantation within a patient.

BACKGROUND OF THE INVENTION

In recent years there has been growing interest in the use of artificial materials, particularly materials formed from polymers, for use in implantable devices that come into contact with bodily tissues or fluids particularly blood. Some examples of such devices are artificial heart valves, stents, and vascular prosthesis. Some medical devices such as implantable stents which are fabricated from a metal have been problematic in fracturing or failing after implantation. Moreover, certain other implantable devices made from polymers have exhibited problems such as increased wall thickness to prevent or inhibit fracture or failure. However, stents having reduced wall thickness are desirable particularly for treating arterial diseases.

Because many polymeric implants such as stents are fabricated through processes such as extrusion or injection molding, such methods typically begin the process by starting with an inherently weak material. In the example of a polymeric stent, the resulting stent may have imprecise geometric tolerances as well as reduced wall thicknesses which may make these stents susceptible to brittle fracture.

A stent which is susceptible to brittle fracture is generally undesirable because of its limited ability to collapse for intravascular delivery as well as its limited ability to expand for placement or positioning within a vessel. Moreover, such polymeric stents also exhibit a reduced level of strength. Brittle fracture is particularly problematic in stents as placement of a stent onto a delivery balloon or within a delivery sheath imparts a substantial amount of compressive force in the material comprising the stent. A stent made of a brittle material may crack or have a very limited ability to collapse or expand without failure. Thus, a certain degree of malleability is desirable for a stent to expand, deform, and maintain its position securely within the vessel.

Accordingly, it is desirable to produce a polymeric substrate having one or more layers which retains its mechanical strength and is sufficiently ductile so as to prevent or inhibit brittle fracture, particularly when utilized as a biocompatible and/or bioabsorbable polymeric stent for implantation within a patient body.

SUMMARY OF THE INVENTION

A number of casting processes described herein may be utilized to develop substrates (e.g., cylindrically shaped substrates, ellipsoid shaped substrates, diamond-shaped substrates, etc.) having a relatively high level of geometric precision and mechanical strength. These polymeric substrates can then be machined using any number of processes (e.g., high-speed laser sources, mechanical machining, etc.) to create devices such as stents having a variety of geometries for implantation within a patient, such as the peripheral or coronary vasculature, etc.

An example of such a casting process is to utilize a dip-coating process. The utilization of dip-coating to create a polymeric substrate having such desirable characteristics results in substrates which are able to retain the inherent properties of the starting materials. This in turn results in substrates having relatively high radial strength, ductility and associated fatigue characteristics which are retained through any additional manufacturing processes for implantation. Additionally, dip-coating the polymeric substrate also allows for the creation of substrates having multiple layers.

The molecular weight of a polymer is typically one of the factors in determining the mechanical behavior of the polymer. With an increase in the molecular weight of a polymer, there is generally a transition from brittle to ductile failure. Ductile materials also have a comparatively higher fatigue life. A mandrel may be utilized to cast or dip-coat the polymeric substrate.

In dip-coating the polymeric substrate, one or more high molecular weight biocompatible and/or bioabsorbable polymers may be selected for forming upon the mandrel. The one or more polymers may be dissolved in a compatible solvent in one or more corresponding containers such that the appropriate solution may be placed under the mandrel. As the substrate may be formed to have one or more layers overlaid upon one another, the substrate may be formed to have a first layer of a first polymer, a second layer of a second polymer, and so on depending upon the desired structure and properties of the substrate. Thus, the various solutions and containers may be replaced beneath the mandrel between dip-coating operations in accordance with the desired layers to be formed upon the substrate such that the mandrel may be dipped sequentially into the appropriate polymeric solution.

Parameters such as the number of times the mandrel is immersed, the sequence and direction of dipping, the duration of time of each immersion within the solution, as well as the delay time between each immersion or the drying or curing time between dips and dipping and/or withdrawal rates of the mandrel to and/or from the solution may each be controlled to result in the desired mechanical characteristics. Formation via the dip-coating process may result in a polymeric substrate having substantially less wall thickness while retaining an increased level of strength in the substrate as compared to an extruded or injection-molded polymeric structure.

The immersion times as well as drying times may be uniform between each immersion or they may be varied as determined by the desired properties of the resulting substrate. Moreover, the substrate may be placed in an oven or dried at ambient temperature between each immersion or after the final immersion to attain a predetermined level of crystals, e.g., 20% to 40%, and a level of amorphous polymeric structure, e.g., 60% to 80%. Each of the layers overlaid upon one another during the dip-coating process are tightly adhered to one another and the wall thicknesses and mechanical properties of each polymer are retained in their respective layer with no limitation on the molecular weight and/or crystalline structure of the polymers utilized.

Dip-coating can be used to impart an orientation between layers (e.g., linear orientation by dipping; radial orientation by spinning the mandrel; etc.) to further enhance the mechanical properties of the formed substrate. As radial strength is a desirable attribute of stent design, post-processing of the formed substrate may be accomplished to impart such attributes. Typically, polymeric stents suffer from having relatively thick walls to compensate for the lack of radial strength, and this in turn reduces flexibility, impedes navigation, and reduces arterial luminal area immediately post implantation. Post-processing may also help to prevent material creep and recoil (creep is a time-dependent permanent deformation that occurs to a specimen under stress, typically under elevated temperatures) which are problems typically associated with polymeric stents.

For post-processing, a predetermined amount of force may be applied to the substrate where such a force may be generated by a number of different methods. One method is by utilizing an expandable pressure vessel placed within the substrate. Another method is by utilizing a braid structure, such as a braid made from a super-elastic or shape memory alloy like NiTi alloy, to increase in size and to apply the desirable degree of force against the interior surface of the substrate.

Yet another method may apply the expansion force by application of a pressurized inert gas such as nitrogen within the substrate lumen. A completed substrate may be placed inside a molding tube which has an inner diameter that is larger than the cast cylinder. A distal end or distal portion of the cast cylinder may be clamped or otherwise closed and a pressure source may be coupled to a proximal end of the cast cylinder. The entire assembly may be positioned over a nozzle which applies heat to either the length of the cast cylinder or to a portion of cast cylinder. The increase in diameter of the cast cylinder may thus realign the molecular orientation of the cast, cylinder to increase its radial strength. After the diameter has been increased, the cast cylinder may be cooled.

Once the processing has been completed on the polymeric substrate, the substrate may be further formed or machined to create a variety of device. One example includes stents created from the cast cylinder by cutting along a length of the cylinder to create a rolled stent for delivery and deployment within the patient vasculature. Another example includes machining a number of portions to create a lattice or scaffold structure which facilitates the compression and expansion of the stent.

In other variations, in forming the stent, the substrate may be first formed at a first diameter, as described herein by immersing a mandrel into at least a first polymeric solution such that at least a first layer of a biocompatible polymer substrate is formed upon the mandrel and has a first diameter defined by the mandrel. In forming the substrate, parameters such as controlling a number of immersions of the mandrel into the first polymeric solution, controlling a duration of time of each immersion of the mandrel, and controlling a delay time between each immersion of the mandrel are controlled. With the substrate initially formed, the first diameter of the substrate may be reduced to a second smaller diameter and processed to form an expandable stent scaffold configured for delivery and deployment within a vessel, wherein the stent scaffold retains one or more mechanical properties of the polymer resin such that the stent scaffold exhibits ductility upon application of a load.

With the stent scaffold formed and heat set to have an initial diameter, it may be reduced to a second delivery diameter and placed upon a delivery catheter for intravascular delivery within a patient body comprising positioning the stent having the second diameter at a target location within the vessel, expanding the stent to a third diameter that is larger than the second diameter (and possibly smaller than the initial diameter) at the target location utilizing an inflation balloon or other mechanism, and allowing the stent to then self-expand into further contact with the vessel at the target location such that the stent self-expands over time back to its initial diameter or until it is constrained from further expansion by the vessel walls.

BRIEF DESCRIPTION OF THE DRAWINGS

FIGS. 3A to 3C show respective partial cross-sectional side and end views of an example of a portion of a multi-layer polymeric substrate formed along the mandrel and the resulting substrate.

DETAILED DESCRIPTION OF THE INVENTION

Figure 1:
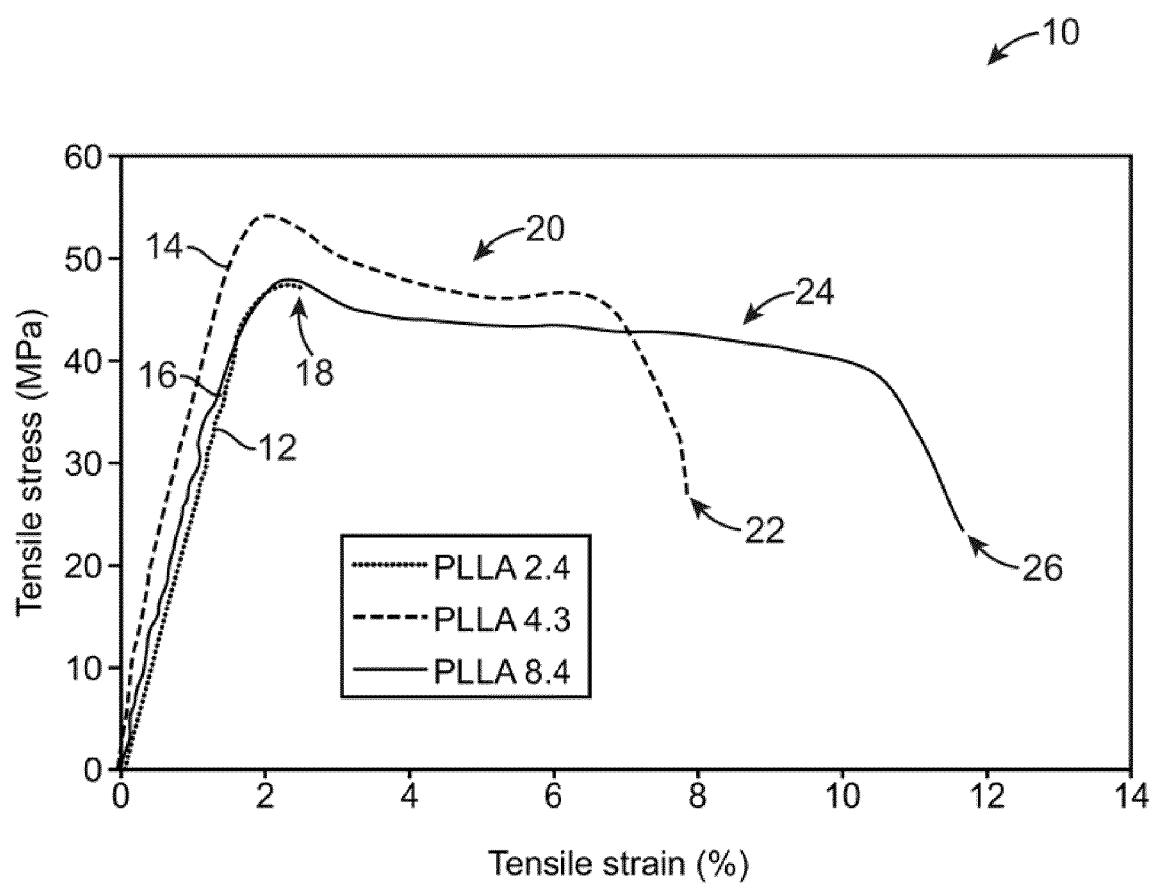
FIG. 1 illustrates a stress-strain plot of polylactic acid (PLLA) at differing molecular weights and their corresponding stress-strain values indicating brittle fracture to ductile failure.

In manufacturing implantable devices from polymeric materials such as biocompatible and/or biodegradable polymers, a number of casting processes described herein may be utilized to develop substrates, e.g., cylindrically shaped substrates, having a relatively high level of geometric precision and mechanical strength. These polymeric substrates can then be machined using any number of processes (e.g., high-speed laser sources, mechanical machining, etc.) to create devices such as stents having a variety of geometries for implantation within a patient, such as the peripheral or coronary vasculature, etc.

An example of such a casting process is to utilize a dip-coating process. The utilization of dip-coating to create a polymeric substrate having such desirable characteristics results in substrates which are able to retain the inherent properties of the starting materials. This in turn results in substrates having a relatively high radial strength which is mostly retained through any additional manufacturing processes for implantation. Additionally, dip-coating the polymeric substrate also allows for the creation of substrates having multiple layers. The multiple layers may be formed from the same or similar materials or they may be varied to include any number of additional agents, such as one or more drugs for treatment of the vessel, as described in further detail below. Moreover, the variability of utilizing multiple layers for the substrate may allow one to control other parameters, conditions, or ranges between individual layers such as varying the degradation rate between layers while maintaining the intrinsic molecular weight and mechanical strength of the polymer at a high level with minimal degradation of the starting materials.

Because of the retention of molecular weight and mechanical strength of the starting materials via the casting or dip-coating process, polymeric substrates may be formed which enable the fabrication of devices such as stents with reduced wall thickness which is highly desirable for the treatment of arterial diseases. Furthermore these processes may produce structures having precise geometric tolerances with respect to wall thicknesses, concentricity, diameter, etc.

One mechanical property in particular which is generally problematic with, e.g., polymeric stents formed from polymeric substrates, is failure via brittle fracture of the device when placed under stress within the patient body. It is generally desirable for polymeric stents to exhibit ductile failure under an applied load rather via brittle failure, especially during delivery and deployment of a polymeric stent from an inflation balloon or constraining sheath, as mentioned above. Percent (%) ductility is generally a measure of the degree of plastic deformation that has been sustained by the material at fracture. A material that experiences very little or no plastic deformation upon fracture is brittle.

The molecular weight of a polymer is typically one of the factors in determining the mechanical behavior of the polymer. With an increase in the molecular weight of a polymer, there is generally a transition from brittle to ductile failure. An example is illustrated in the stress-strain plot 10 which illustrate the differing mechanical behavior resulting from an increase in molecular weight. The stress-strain curve 12 of a sample of polylactic acid (PLLA) 2.4 shows a failure point 18 having a relatively low tensile strain percentage at a high tensile stress level indicating brittle failure. A sample of PLLA 4.3, which has a relatively higher molecular weight than PLLA 2.4, illustrates a stress-strain curve 14 which has a region of plastic failure 20 after the onset of yielding and a failure point 22 which has a relatively lower tensile stress value at a relatively higher tensile strain percentage indicating a degree of ductility. Yield occurs when a material initially departs from the linearity of a stress-strain curve and experiences an elastic-plastic transition.

A sample of PLLA 8.4, which has yet a higher molecular weight than PLLA 4.3, illustrates a stress-strain curve 16 which has a longer region of plastic failure 24 after the onset of yielding. The failure point 26 also has a relatively lower tensile stress value at a relatively higher tensile strain percentage indicating a degree of ductility. Thus, a high-strength tubular material which exhibits a relatively high degree of ductility may be fabricated utilizing polymers having a relatively high molecular weight (e.g., PLLA 8.4, PLLA with 8.28 IV, etc.). Such a tubular material may be processed via any number of machining processes to form an implantable device such as a stent which exhibits a stress-strain curve which is associated with the casting or dip-coating process described herein. The resultant device can be subjected to relatively high levels of strain without fracturing.

Figure 2A:
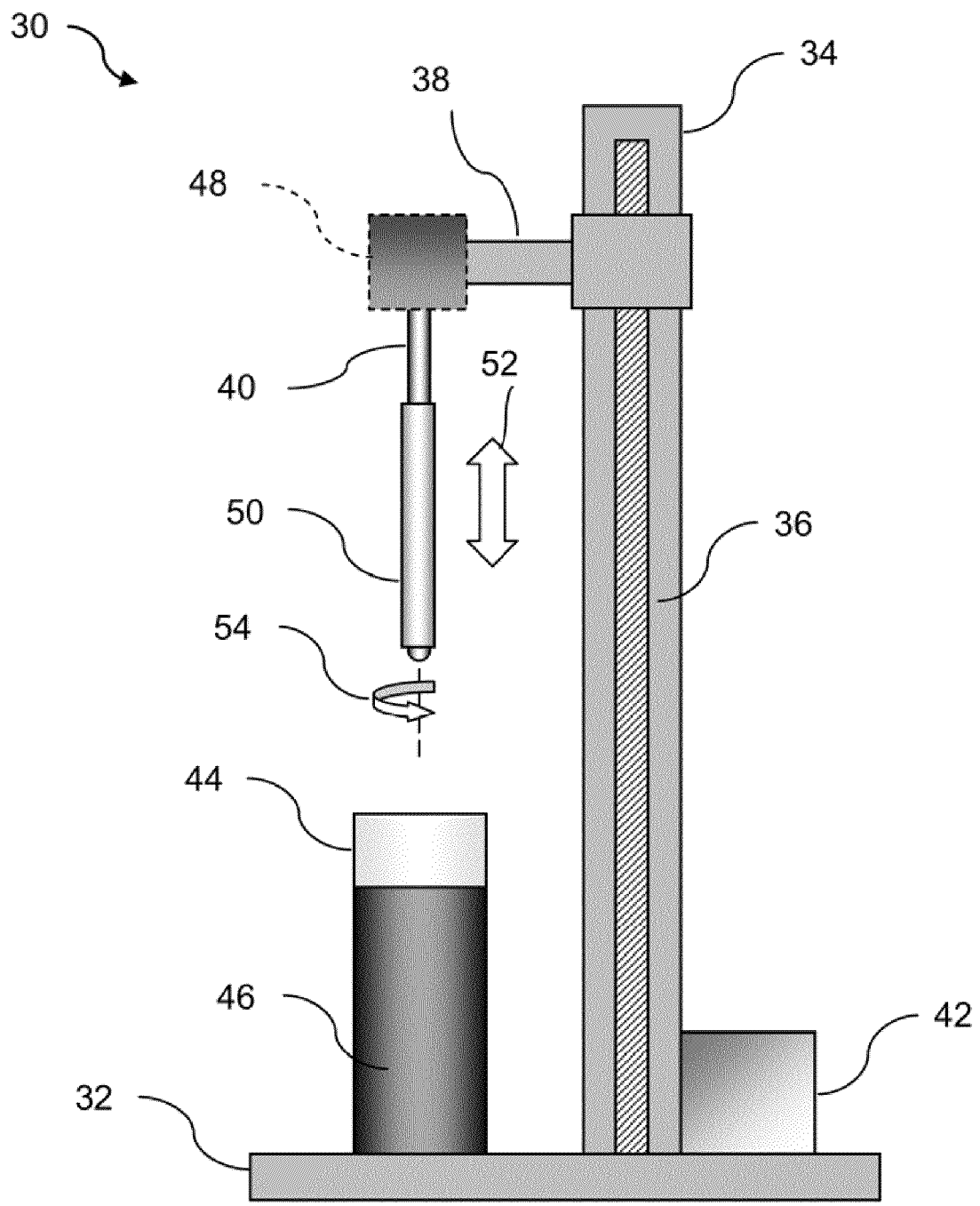
FIG. 2A illustrates an example of a dip-coating machine which may be utilized to form a polymeric substrate having one or more layers formed along a mandrel.

An example of a mandrel which may be utilized to cast or dip-coat the polymeric substrate is illustrated in the side view of FIG. 2A. Generally, dip coating assembly 30 may be any structure which supports the manufacture of the polymeric substrate in accordance with the description herein. A base 32 may support a column 34 which houses a drive column 36 and a bracket arm 38. Motor 42 may urge drive column 36 vertically along column 34 to move bracket arm 38 accordingly. Mandrel 40 may be attached to bracket arm 38 above container 44 which may be filled with a polymeric solution 46 (e.g., PLLA, PLA, PLGA, etc.) into which mandrel 40 may be dipped via a linear motion 52. The one or more polymers may be dissolved in a compatible solvent in one or more corresponding containers 44 such that the appropriate solution may be placed under mandrel 40. An optional motor 48 may be mounted along bracket arm 38 or elsewhere along assembly 30 to impart an optional rotational motion 54 to mandrel 40 and the substrate 50 formed along mandrel 40 to impart an increase in the circumferential strength of substrate 50 during the dip-coating process, as described in further detail below.

The assembly 30 may be isolated on a vibration-damping or vibrationally isolated table to ensure that the liquid surface held within container 44 remains completely undisturbed to facilitate the formation of a uniform thickness of polymer material along mandrel 40 and/or substrate 50 with each deposition The entire assembly 30 or just a portion of the assembly such as the mandrel 40 and polymer solution may be placed in an inert environment such as a nitrogen gas environment while maintaining a very low relative humidity (RH) level, e.g., less than 30% RH, and appropriate dipping temperature, e.g., at least 20° C. below the boiling point of the solvent within container 44 so as to ensure adequate bonding between layers of the dip-coated substrate. Multiple mandrels may also be mounted along bracket arm 38 or directly to column 34.

Various drying methods may be utilized, e.g., convection, infrared, or other conventional drying techniques within a controlled environment are generally desirable as high humidity levels with high temperatures can induce hydrolysis which affects the crystallinity level and mechanical properties of the substrates during drying. For instance, PLA 8.4 substrates have a percentage of crystallinity level between, e.g., 20% to 40% or more particularly between 27% to 35%, which generally exhibit good ductility during tensile tests. If the substrates have a crystallinity that approaches 60% (which is typically the crystallinity of resin), the substrates will generally exhibit brittle failure.

Convection drying may be typically employed to uniformly heat and dry the substrates to a residual solvent level of, e.g., less than 100 ppm, while vacuum drying and/or infrared drying can be employed to shorten or reduce the typical drying time of 10 or up to 40 days depending on type of polymers used. Infrared drying can be employed to dry the surface layers at a temperature which is higher than a drying temperature of the inner layers which may contain heat sensitive drugs. In this case, the drugs within the inner layers are prevented or inhibited from degrading within the matrix. Moreover, infrared drying may prevent or inhibit the inner layers from thermal degradation if a different polymer of different glass transition temperature is used whereas convection drying for such a combination substrate may be less desirable. Generally, the drying temperature maybe performed at 5° to 10° C. below or higher than the glass transition temperature.

The mandrel 40 may be sized appropriately and define a cross-sectional geometry to impart a desired shape and size to the substrate 50. Mandrel 40 may be generally circular in cross section although geometries may be utilized as desired. In one example, mandrel 40 may define a circular geometry having a diameter ranging from 1 mm to 20 mm to form a polymeric substrate having a corresponding inner diameter. Moreover, mandrel 40 may be made generally from various materials which are suitable to withstand dip-coating processes, e.g., stainless steel, copper, aluminum, silver, brass, nickel, titanium, etc. The length of mandrel 40 that is dipped into the polymer solution may be optionally limited in length by, e.g., 50 cm, to ensure that an even coat of polymer is formed along the dipped length of mandrel 40 to limit the effects of gravity during the coating process. Mandrel 40 may also be made from a polymeric material which is lubricious, strong, has good dimensional stability, and is chemically resistant to the polymer solution utilized for dip-coating, e.g., fluoropolymers, polyacetal, polyester, polyamide, polyacrylates, etc.

Mandrel 40 may be made alternatively from a shape memory material, such as a shape memory polymer (SMP) or a shape memory alloy, to assist in the removal of a substrate 50 from the mandrel 40 by inducing a temporary shape of a uniform tubular form in the mandrel 40 during dipping. Additionally and/or alternatively, a layer of SMP may be utilized as a layer for dip coating substrate 50. After drying, the substrate 50 and mandrel 40 maybe subjected to temperature change, $T>T_g$ by 50 to 10° C. to induce a small deformation of less than 5% in the mandrel 40 to assist in the removal of the substrate 50 and/or for delaminating the SMP layer to further assist in removing the substrate 50. The mandrel 40 may be comprised of various shape memory alloys, e.g., Nickel-Titanium, and various SMPs may comprise, e.g., physically cross-linked polymers or chemically cross-linked polymers etc. Examples of physically cross-linked polymers may include polyurethanes with ionic or mesogenic components made by prepolymer methods. Other block copolymers which may also be utilized may include, e.g., block copolymers of polyethyleneterephrhalate (PET) and polyethyleneoxide (PEO), block copolymers containing polystyrene and poly(1,4-butadiene), ABA triblock copolymer made from poly(2-methyl-2-oxazoline) and poly(Tetrahydrofuran), etc.

Moreover, mandrel 40 may be made to have a smooth surface for the polymeric solution to form upon. In other variations, mandrel 40 may define a surface that is coated with a material such as polytetrafluoroethylene to enhance removal of the polymeric substrate formed thereon. In yet other variations, mandrel 40 may be configured to define any number of patterns over its surface, e.g., either over its entire length or just a portion of its surface, that can be mold-transferred during the dip-coating process to the inner surface of the first layer of coating of the dip-coated substrate tube. The patterns may form raised or depressed sections to form various patterns such as checkered, cross-hatched, cratered, etc. that may enhance endothelialization with the surrounding tissue after the device is implanted within a patient, e.g., within three to nine months of implantation.

The direction that mandrel 40 is dipped within polymeric solution 46 may also be alternated or changed between layers of substrate 50. In forming substrates having a length ranging from, e.g., 1 cm to 40 cm or longer, substrate 50 may be removed from mandrel 40 and replaced onto mandrel 40 in an opposite direction before the dipping process is continued. Alternatively, mandrel 40 may be angled relative to bracket arm 38 and/or polymeric solution 46 during or prior to the dipping process.

Figure 2B:
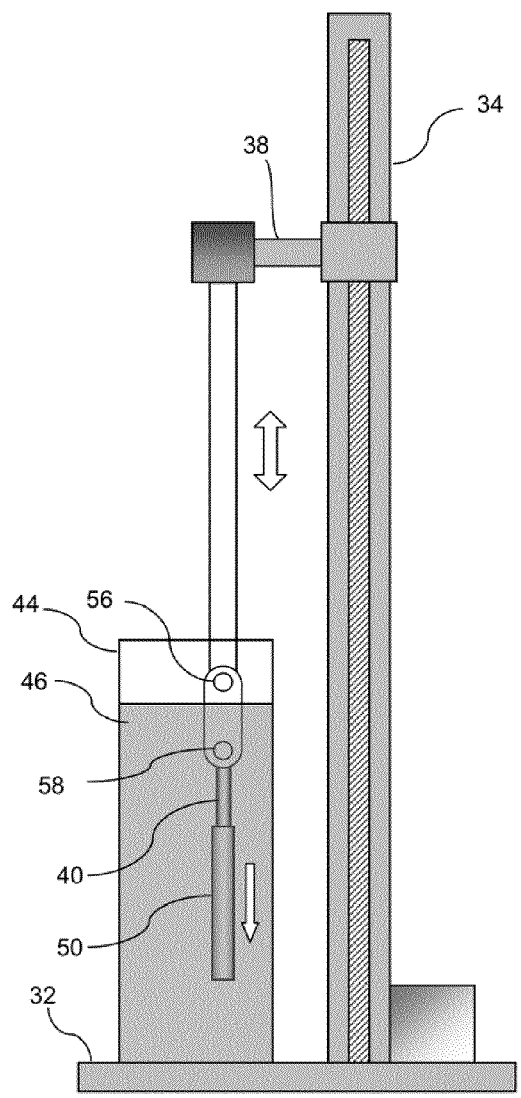
FIGS. 2B and 2C illustrate another example of a dip-coating assembly having one or more articulatable linkages to adjust a dipping direction of the mandrel.
Figure 2C:
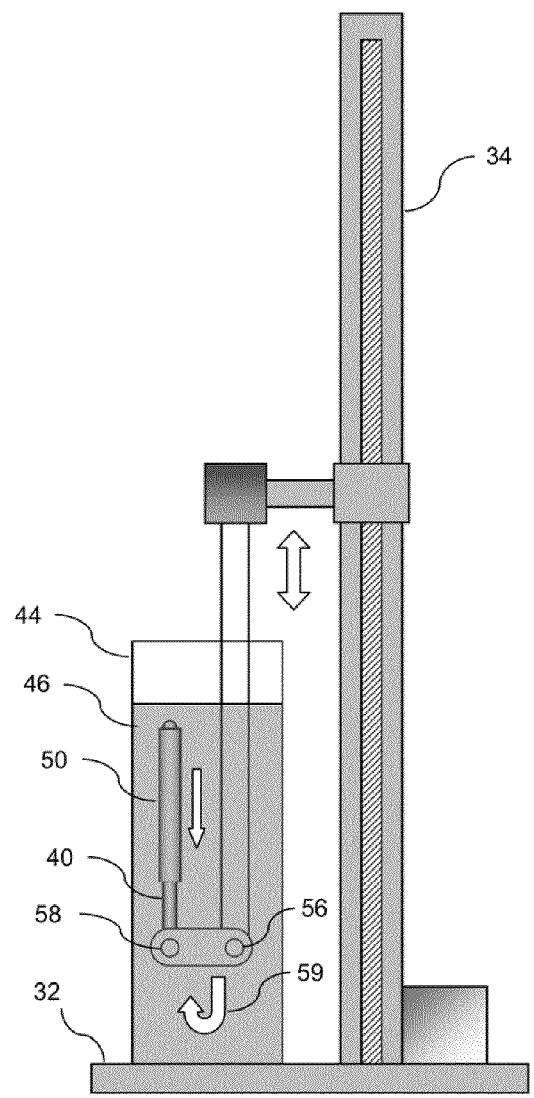

This may also be accomplished in yet another variation by utilizing a dipping assembly as illustrated in FIGS. 2B and 2C to achieve a uniform wall thickness throughout the length of the formed substrate 50 per dip. For instance, after 1 to 3 coats are formed in a first dipping direction, additional layers formed upon the initial layers may be formed by dipping mandrel 40 in a second direction opposite to the first dipping direction, e.g., angling the mandrel 40 anywhere up to 180° from the first dipping direction. This may be accomplished in one example through the use of one or more pivoting linkages 56, 58 connecting mandrel 40 to bracket arm 38, as illustrated. The one or more linkages 56, 58 may maintain mandrel 40 in a first vertical position relative to solution 46 to coat the initial layers of substrate 50, as shown in FIG. 2B. Linkages 56, 58 may then be actuated to reconfigure mandrel 40 from its first vertical position to a second vertical position opposite to the first vertical position, as indicated by direction 59 in FIG. 2C. With repositioning of mandrel 40 complete, the dipping process may be resumed by dipping the entire linkage assembly along with mandrel 40 and substrate 50. In this manner, neither mandrel 40 nor substrate 50 needs to be removed and thus eliminates any risk of contamination. Linkages 56, 58 may comprise any number of mechanical or electromechanical pivoting and/or rotating mechanisms as known in the art.

Dipping mandrel 40 and substrate 50 in different directions may also enable the coated layers to have a uniform thickness throughout from its proximal end to its distal end to help compensate for the effects of gravity during the coating process. These values are intended to be illustrative and are not intended to be limiting in any manner. Any excess dip-coated layers on the linkages 56, 58 may simply be removed from mandrel 40 by breaking the layers. Alternating the dipping direction may also result in the polymers being oriented alternately which may reinforce the tensile strength in the axial direction of the dip coated tubular substrate 50.

With dip-coating assembly 30, one or more high molecular weight biocompatible and/or bioabsorbable polymers may be selected for forming upon mandrel 40. Examples of polymers which may be utilized to form the polymeric substrate may include, but is not limited to, polyethylene, polycarbonates, polyamides, polyesteramides, polyetheretherketone, polyacetals, polyketals, polyurethane, polyolefin, or polyethylene terephthalate and degradable polymers, for example, polylactide (PLA) including poly-L-lactide (PLLA), poly (DL-Lactide), poly-glycolide (PGA), poly(lactide-co-glycolide) (PLGA) or polycaprolactone, caprolactones, polydioxanones, polyanhydrides, polyorthocarbonates, polyphosphazenes, chitin, chitosan, poly(amino acids), and polyorthoesters, and copolymers, terpolymers and combinations and mixtures thereof.

Other examples of suitable polymers may include synthetic polymers, for example, oligomers, homopolymers, and co-polymers, acrylics such as those polymerized from methyl cerylate, methyl methacrylate, acryli acid, methacrylic acid, acrylamide, hydroxyethyl acrylate, hydroxyethyl methacrylate, glyceryl serylate, glyceryl methacrylate, methacrylamide and ethacrylamide; vinyls such as styrene, vinyl chloride, binaly pyrrolidone, polyvinyl alcohol, and vinyls acetate; polymers formed of ethylene, propylene, and tetrifluoroethylene. Further examples may include nylons such as polycoprolactam, polylauryl lactam, polyjexamethylene adipamide, and polyexamethylene dodecanediamide, and also polyurethanes, polycarbonates, polyamides, polysulfones, poly(ethylene terephthalate), polyactic acid, polyglycolic acid, polydimethylsiloxanes, and polyetherketones.

Examples of biodegradable polymers which can be used for dip-coating process are polylactide (PLA), polyglycolide (PGA), poly(lactide-co-glycolide) (PLGA), poly(e-caprolactone), polydioxanone, polyanhydride, trimethylene carbonate, poly($\beta$-hydroxybutyrate), poly(g-ethyl glutamate), poly (DTH iminocarbonate), poly(bisphenol A iminocarbonate), poly(ortho ester), polycyanoacrylate, and polyphosphazene, and copolymers, terpolymers and combinations and mixtures thereof. There are also a number of biodegradable polymers derived from natural sources such as modified polysaccharides (cellulose, chitin, chitosan, dextran) or modified proteins (fibrin, casein).

Other examples of suitable polymers may include synthetic polymers, for example, oligomers, homopolymers, and co-polymers, acrylics such as those polymerized from methyl cerylate, methyl methacrylate, acryl acid, methacrylic acid, acrylamide, hydroxyethyl acrylate, hydroxyethyl methacrylate, glyceryl serylate, glyceryl methacrylate, methacrylamide and ethacrylamide; vinyls such as styrene, vinyl chloride, binaly pyrrolidone, polyvinyl alcohol, and vinyls acetate; polymers formed of ethylene, propylene, and tetrifluoroethylene. Further examples may include nylons such as polycoprolactam, polylauryl lactam, polyjexamethylene adipamide, and polyexamethylene dodecanediamide, and also polyurethanes, polycarbonates, polyamides, polysulfones, poly(ethylene terephthalate), polyacetals, polyketals, polydimethylsiloxanes, and polyetherketones.

These examples of polymers which may be utilized for forming the substrate are not intended to be limiting or exhaustive but are intended to be illustrative of potential polymers which may be used. As the substrate may be formed to have one or more layers overlaid upon one another, the substrate may be formed to have a first layer of a first polymer, a second layer of a second polymer, and so on depending upon the desired structure and properties of the substrate. Thus, the various solutions and containers may be replaced beneath mandrel 40 between dip-coating operations in accordance with the desired layers to be formed upon the substrate such that the mandrel 40 may be dipped sequentially into the appropriate polymeric solution.

Depending upon the desired wall thickness of the formed substrate, the mandrel 40 may be dipped into the appropriate solution as determined by the number of times the mandrel 40 is immersed, the duration of time of each immersion within the solution, as well as the delay time between each immersion or the drying or curing time between dips. Additionally, parameters such as the dipping and/or withdrawal rate of the mandrel 40 from the polymeric solution may also be controlled to range from, e.g., 5 mm/min to 1000 mm/min. Formation via the dip-coating process may result in a polymeric substrate having half the wall thickness while retaining an increased level of strength in the substrate as compared to an extruded polymeric structure. For example, to form a substrate having a wall thickness of, e.g., 200 µm, built up of multiple layers of polylactic acid, mandrel 40 may be dipped between, e.g., 2 to 20 times or more, into the polymeric solution with an immersion time ranging from, e.g., 15 seconds (or less) to 240 minutes (or more). Moreover, the substrate and mandrel 40 may be optionally dried or cured for a period of time ranging from, e.g., 15 seconds (or less) to 60 minutes (or more) between each immersion. These values are intended to be illustrative and are not intended to be limiting in any manner.

Aside from utilizing materials which are relatively high in molecular weight, another parameter which may be considered in further increasing the ductility of the material is its crystallinity, which refers to the degree of structural order in the polymer. Such polymers may contain a mixture of crystalline and amorphous regions where reducing the percentage of the crystalline regions in the polymer may further increase the ductility of the material. Polymeric materials not only having a relatively high molecular weight but also having a relatively low crystalline percentage may be utilized in the processes described herein to form a desirable tubular substrate.

The following Table 1 show examples of various polymeric materials (e.g., PLLA IV 8.28 and PDLLA 96/4) to illustrate the molecular weights of the materials in comparison to their respective crystallinity percentage. The glass transition temperature, $T_g$, as well as melting temperature, $T_m$, are given as well. An example of PLLA IV 8.28 is shown illustrating the raw resin and tube form as having the same molecular weight, $M_w$, of $1.70 \times 10^6$ gram/mol. However, the crystallinity percentage of PLLA IV 8.28 Resin is 61.90% while the corresponding Tube form is 38.40%. Similarly for PDLLA 96/4, the resin form and tube form each have a molecular weight, $M_w$, of $9.80 \times 10^5$ gram/mol; however, the crystallinity percentages are 46.20% and 20.90%, respectively.

TABLE 1

Various polymeric materials and their respective crystallinity percentages.

| Material | $T_g$ (° C.) | $T_m$ (° C.) | Crystallinity (%) | $M_w$ (gram/mol) |
|---|---|---|---|---|
| PLLA IV8.28 Resin | 72.5 | 186.4 | 61.90% | $1.70 \times 10^6$ |
| PLLA IV8.28 Tubes | 73.3 | 176.3 | 38.40% | $1.70 \times 10^6$ |
| PDLLA 96/4 Resin | 61.8 | 155.9 | 46.20% | $9.80 \times 10^5$ |
| PDLLA 96/4 Tubes | 60.3 | 146.9 | 20.90% | $9.80 \times 10^5$ |

As the resin is dip coated to form the tubular substrate through the methods described herein, the drying procedures and processing helps to preserve the relatively high molecular weight of the polymer from the starting material and throughout processing to substrate and stent formation. Moreover, the drying processes in particular may facilitate the formation of desirable crystallinity percentages, as described above. Furthermore, the molecular weight and crystallinity percentages, which define the strength of the substrate, are uniform within each layer as well as throughout the entire structure thereby creating a substrate that is isotropic in nature.

The resulting substrate, and the stent formed from the substrate, generally exhibits an equivalent strength in all directions. For example, the resulting stent may exhibit a radial strength which is equal to an axial or tangential strength of the stent. This feature may allow for the substrate and stent to handle loads imparted by the surrounding tissue at any number of angles. This may be particularly desirable in peripheral vessels such as the superficial femoral artery (SFA), where an implanted stent needs to be able to resist a complex and multi-axis loading condition. As strength in tubular polymeric structures are generally directional and in the case of stents, the radial strength is typically higher than the relative strengths in either the axial and tangential direction. Accordingly, the preservation of the starting polymer molecular weight helps to result in a stent having equivalent strength in all directions.

The isotropic property cannot be achieved by such processes as injection molding, extrusion and blow molding. The injection molding and extrusion processes induce axial strength while the blow molding process induces a circumferential orientation. As the result, stents that are fabricated using these processes have a preferential strength specific to the axis of orientation. In many stent designs, the isotropic material characteristics are advantageous since deformation of such material are more predictable and the prosthesis created from such substrates may have a more uniform distribution of stresses under loading conditions.

Aside from the crystallinity of the materials, the immersion times as well as drying times may be uniform between each immersion or they may be varied as determined by the desired properties of the resulting substrate. Moreover, the substrate may be placed in an oven or dried at ambient temperature between each immersion or after the final immersion to attain a predetermined level of crystals, e.g., 20% to 40%, and a level of amorphous polymeric structure, e.g., 60% to 80%. Each of the layers overlaid upon one another during the dip-coating process are tightly adhered to one another and the mechanical properties of each polymer are retained in their respective layer with no limitation on the molecular weight of the polymers utilized. The dipping process also allows the operator to control molecular weight and crystallinity of the tubular structure which becomes the base for the resulting prosthesis. Depending on the molecular weight and crystallinity combination chosen, the resulting prosthesis may be able to provide high radial strength (e.g., 10 N per 1 cm length at 20% compression), withstand considerable amount of strain without fracturing (e.g., 150% strain), and exhibit high fatigue life under physiological conditions (e.g., 10 million cycles under radial pulse load).

Varying the drying conditions of the materials may also be controlled to effect desirable material parameters. The polymers may be dried at or above the glass transition temperature (e.g., 10° to 20° C. above the glass transition temperature, $T_g$) of the respective polymer to effectively remove any residual solvents from the polymers to attain residual levels of less than 100 ppm, e.g., between 20 to 100 ppm. Positioning of the polymer substrate when drying is another factor which may be controlled as affecting parameters, such as geometry, of the tube. For instance, the polymer substrate may be maintained in a drying position such that the substrate tube is held in a perpendicular position relative to the ground such that the concentricity of the tubes is maintained. The substrate tube may be dried in an oven at or above the glass transition temperature, as mentioned, for a period of time ranging anywhere from, e.g., 10 days to 30 days or more. However, prolonged drying for a period of time, e.g., greater than 40 days, may result in thermal degradation of the polymer material.

Additionally and/or optionally, a shape memory effect may be induced in the polymer during drying of the substrate. For instance, a shape memory effect may be induced in the polymeric tubing to set the tubular shape at the diameter that was formed during the dip-coating process. An example of this is to form a polymeric tube by a dip-coating process described herein at an outer diameter of 5 mm and subjecting the substrate to temperatures above its glass transition temperature, $T_g$. At its elevated temperature, the substrate may be elongated, e.g., from a length of 5 cm to 7 cm, while its outer diameter of 5 mm is reduced to 3 mm. Of course, these examples are merely illustrative and the initial diameter may generally range anywhere from, e.g., 3 mm to 10 mm, and the reduced diameter may generally range anywhere from, e.g., 1.5 mm to 5 mm, provided the reduced diameter is less than the initial diameter.

Once lengthened and reduced in diameter, the substrate may be quenched or cooled in temperature to a sub-$T_g$ level, e.g., about 20° C. below its $T_g$, to allow for the polymeric substrate to transition back to its glass state. This effectively imparts a shape memory effect of self-expansion to the original diameter of the substrate. When such a tube (or stent formed from the tubular substrate) is compressed or expanded to a smaller or larger diameter and later exposed to an elevated temperature, over time the tube (or stent) may revert to its original 5 mm diameter. This post processing may also be useful for enabling self-expansion of the substrate after a process like laser cutting (e.g., when forming stents or other devices for implantation within the patient) where the substrate tube is typically heated to its glass transition temperature, $T_g$.

An example of a substrate having multiple layers is illustrated in FIGS. 3A and 3B which show partial cross-sectional side views of an example of a portion of a multi-layer polymeric substrate formed along mandrel 40 and the resulting substrate. Substrate 50 may be formed along mandrel 40 to have a first layer 60 formed of a first polymer, e.g., poly(1-lactide). After the formation of first layer 60, an optional second layer 62 of polymer, e.g., poly(L-lactide-co-glycolide), may be formed upon first layer 60. Yet another optional third layer 64 of polymer, e.g., poly(d,l-lactide-co-glycolide), may be formed upon second layer 62 to form a resulting substrate defining a lumen 66 therethrough which may be further processed to form any number of devices, such as a stent. One or more of the layers may be formed to degrade at a specified rate or to elute any number of drugs or agents.

An example of this is illustrated in the cross-sectional end view of FIG. 3C, which shows an exemplary substrate having three layers 60, 62, 64 formed upon one another, as above. In this example, first layer 60 may have a molecular weight of $M_{n1}$, second layer 62 may have a molecular weight of $M_{n2}$, and third layer 64 may have a molecular weight of $M_{n3}$. A stent fabricated from the tube may be formed such that the relative molecular weights are such where $M_{n1} > M_{n2} > M_{n3}$ to achieve a preferential layer-by-layer degradation through the thickness of the tube beginning with the inner first layer 60 and eventually degrading to the middle second layer 62 and finally to the outer third layer 64 when deployed within the patient body. Alternatively, the stent may be fabricated where the relative molecular weights are such where $M_{n1} < M_{n2} < M_{n3}$ to achieve a layer-by-layer degradation beginning with the outer third layer 64 and degrading towards the inner first layer 60. This example is intended to be illustrative and fewer than or more than three layers may be utilized in other examples. Additionally, the molecular weights of each respective layer may be altered in other examples to vary the degradation rates along different layers, if so desired.

For instance, the molecular weight of different layers can also be tailored, e.g. when the first outer layer (with the minimum molecular weight $M_{n1}$) degrades to certain levels, large amounts of oligomers or monomers are formed and the degradation rates of the layers are accelerated due to these low molecular weight degradation products diffused into the layers. By selecting different polymers to form the composition of this outer layer, the time needed to trigger this accelerated degradation of the other layers may be tailored. For example, any of the layers (such as the outer layer or inner layer) may be a co-polymer of 50% PLA/50% PGA where a degradation rate of the PGA is relatively faster than a degradation rate of the PLA. Thus, a layer formed of this co-polymer may have the PGA degrade relatively faster than the PLA, which in turn accelerates the degradation of the PLA itself. Alternatively or additionally, a single layer such as the outer layer may be made from such a co-polymer where degradation of the PGA in the outer layer may accelerate not only the outer layer but also the inner layer as well. Other variations may be accomplished as well depending upon the desired degradation rate and order of degradation between differing layers.

Moreover, any one or more of the layers may be formed to impart specified mechanical properties to the substrate 50 such that the composite mechanical properties of the resulting substrate 50 may specifically tuned or designed. Additionally, although three layers are illustrated in this example, any number of layers may be utilized depending upon the desired mechanical properties of the substrate 50.

Moreover, as multiple layers may be overlaid one another in forming the polymeric substrate, specified layers may be designated for a particular function in the substrate. For example, in substrates which are used to manufacture polymeric stents, one or more layers may be designed as load-bearing layers to provide structural integrity to the stent while certain other layers may be allocated for drug-loading or eluting. Those layers which are designated for structural support may be formed from high-molecular weight polymers, e.g., PLLA or any other suitable polymer described herein, to provide a high degree of strength by omitting any drugs as certain pharmaceutical agents may adversely affect the mechanical properties of polymers. Those layers which are designated for drug-loading may be placed within, upon, or between the structural layers.

An example of utilizing layer-specific substrates may include the incorporation of one or more bio-beneficial layers that can be used to reduce the risk of blood interaction with an internal layer of a prosthesis such as the formation of thrombosis. Representative bio-beneficial materials include, but are not limited to, polyethers such as poly(ethylene glycol), copoly(ether-esters) (e.g. PEO/PLA), polyalkylene oxides such as poly(ethylene oxide), poly(propylene oxide), poly (ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol)acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TM-SPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), molecules such as fibrin, fibrinogen, cellulose, starch, collagen, dextran, dextrin, hyaluronic acid, fragments and derivatives of hyaluronic acid, heparin, fragments and derivatives of heparin, glycosaminoglycan (GAG), GAG derivatives, polysaccharide, elastin, chitosan, alginate, silicones, PolyActive, and combinations thereof. In some embodiments, a coating described herein can exclude any one of the aforementioned polymers. The term PolyActive refers to a block copolymer having flexible poly (ethylene glycol) and poly(butylene terephthalate) blocks (PEGT/PBT). PolyActive is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In another variation, the bio-beneficial material can be a polyether such as poly(ethylene glycol) (PEG) or polyalkylene oxide. Bio-beneficial polymers that can be used to attract endothelium cells can also be coated as this first layer. These polymers, such as NO-generating polymers which may synthesized using the following strategy: (1) dispersed non-covalently bound small molecules where the diazeniumdiolate group is attached to amines in low molecular weight compounds; (2) diazeniumdiolate groups covalently bound to pendent polymer side-chains; and (3) covalently bound diazeniumdiolate groups directly to the polymer backbone. Such polymers may use diethylamine (DEA/N2O2) and diazeniumdiolated-spermine (SPER/N2O2) as the non-covalently bound species blended into both poly(ethylene glycol) (PEG) and polycaprolactone, grafting dipropylenetriamine onto a polysaccharide and by treating polyethyleneimine (PEI) with NO to form a diazeniumdiolate NO donor covalently linked directly to the polymer backbone, and 4) NO-donor that has been utilized in developing NO-releasing polymers are S-nitrosothiols (RSNOs). (Frost et al., Biomaterials, 2005, 26(14), page 1685).

In yet another example, a relatively higher molecular weight PLLA "backbone" layer, i.e., a layer which provides structural strength to a prosthesis, may be coupled with one or more various layers of other types of polymeric materials, such as poly-ε-caprolactone (PCL) or a copolymer of PCL. The backbone layer may provide strength while the PCL layer provides overall ductility to the prosthesis. The combination of layers provides a structure having both high strength and ductility. Of course, other combinations of various materials may be combined depending upon the desired resulting characteristics. For instance, another example may include a prosthesis having an inner layer made of PCL or other elastomeric polymers with a relatively high coefficient of friction. When the prosthesis is ultimately crimped onto an intravascular delivery balloon, this relatively high friction inner layer may prevent or inhibit lateral movement of the prosthesis relative to the inflation balloon to enhance stent retention on the delivery device.

Additionally, multiple layers of different drugs may be loaded within the various layers. The manner and rate of drug release from multiple layers may depend in part upon the degradation rates of the substrate materials. For instance, polymers which degrade relatively quickly may release their drugs layer-by-layer as each successive layer degrades to expose the next underlying layer. In other variations, drug release may typically occur from a multilayer matrix via a combination of diffusion and degradation. In one example, a first layer may elute a first drug for, e.g., the first 30 to 40 days after implantation. Once the first layer has been exhausted or degraded, a second underlying layer having a second drug may release this drug for the next 30 to 40 days, and so on if so desired. In the example of FIG. 3B, for a stent (or other implantable device) manufactured from substrate 50, layer 64 may contain the first drug for release while layer 62 may contain the second drug for release after exhaustion or degradation of layer 64. The underlying layer 60 may omit any pharmaceutical agents to provide uncompromised structural support to the entire structure.

In other examples, rather than having each successive layer elute its respective drug, each layer 62, 64 (optionally layer 60 as well), may elute its respective drug simultaneously or at differing rates via a combination of diffusion and degradation. Although three layers are illustrated in this example, any number of layers may be utilized with any practicable combination of drugs for delivery. Moreover, the release kinetics of each drug from each layer may be altered in a variety of ways by changing the formulation of the drug-containing layer.

Examples of drugs or agents which may be loaded within certain layers of substrate 50 may include one or more antipoliferative, antineoplastic, antigenic, anti-inflammatory, and/or antirestenotic agents. The therapeutic agents may also include antilipid, antimitotics, metalloproteinase inhabitors, anti-sclerosing agents. Therapeutic agents may also include peptides, enzymes, radio isotopes or agents for a variety of treatment options. This list of drugs or agents is presented to be illustrative and is not intended to be limiting.

Similarly certain other layers may be loaded with radio-opaque substances such as platinum, gold, etc. to enable visibility of the stent under imaging modalities such as fluoroscopic imaging. Radio-opaque substances like tungsten, platinum, gold, etc. can be mixed with the polymeric solution and dip-coated upon the substrate such that the radio-opaque substances form a thin sub-micron thick layer upon the substrate. The radio-opaque substances may thus become embedded within layers that degrade in the final stages of degradation or within the structural layers to facilitate stent visibility under an imaging modality, such as fluoroscopy, throughout the life of the implanted device before fully degrading or losing its mechanical strength. Radio-opaque marker layers can also be dip-coated at one or both ends of substrate 50, e.g., up to 0.5 mm from each respective end. Additionally, the radio-opaque substances can also be spray-coated or cast along a portion of the substrate 50 between its proximal and distal ends in a radial direction by rotating mandrel 40 when any form of radio-opaque substance is to be formed along any section of length of substrate 50. Rings of polymers having radio-opaque markers can also be formed as part of the structure of the substrate 50.

Figure 4A:
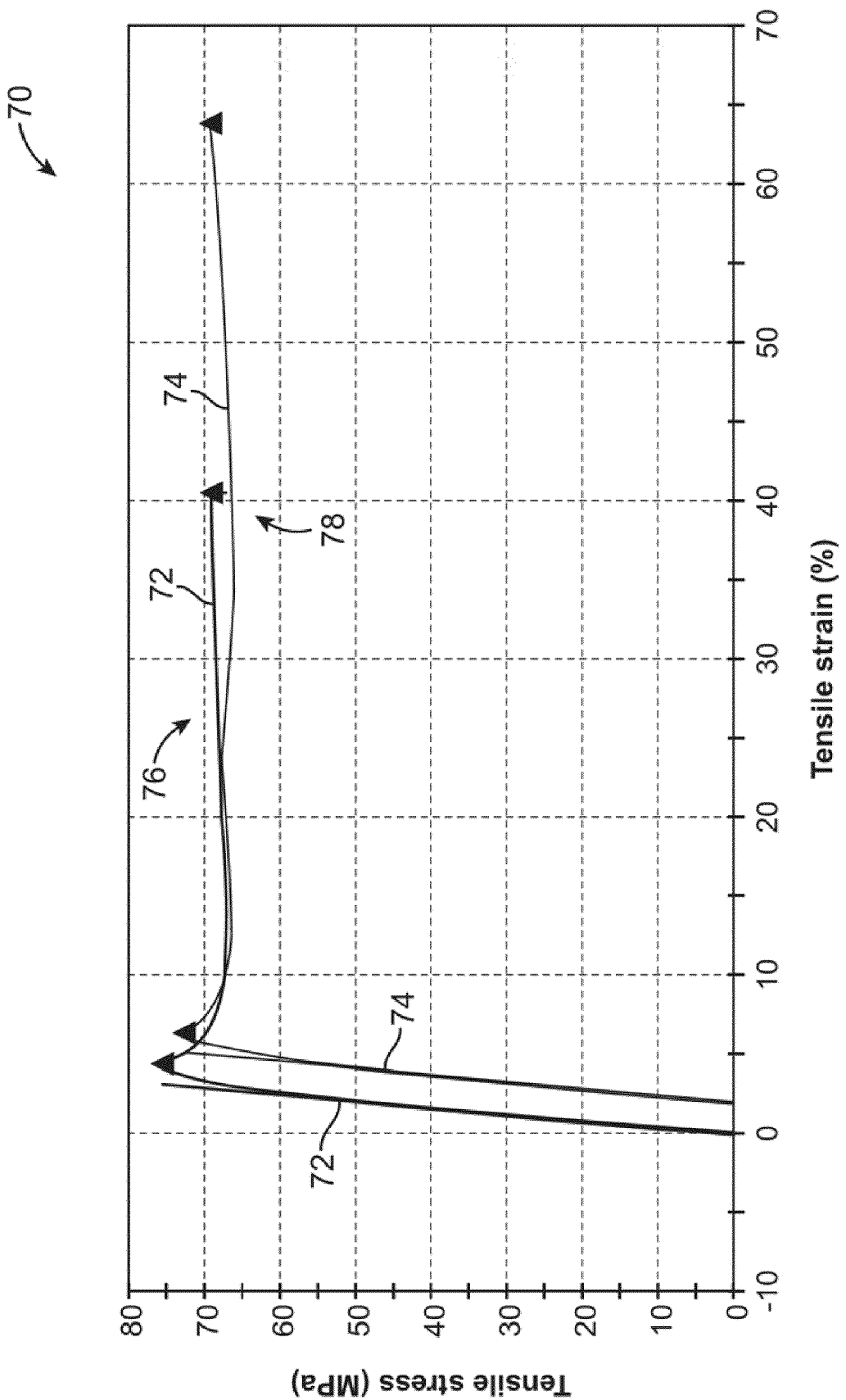
FIG. 4A illustrates an example of a resulting stress-strain plot of various samples of polymeric substrates formed by a dip-coating process and the resulting plots indicating ductile failure.

In an experimental example of the ductility and retention of mechanical properties, PLLA with Iv 8.4 (high molecular weight) was obtained and tubular substrates were manufactured utilizing the dip-coating process described herein. The samples were formed to have a diameter of 5 mm with a wall thickness of 200 µm and were comprised of 6 layers of PLLA 8.4. The mandrel was immersed 6 times into the polymeric solution and the substrates were dried or cured in an oven to obtain a 60% crystalline structure. At least two samples of tubular substrates were subjected to tensile testing and stress-strain plot 70 was generated from the stress-strain testing, as shown in FIG. 4A.

As shown in plot 70, a first sample of PLLA 8.4 generated a stress-strain curve 72 having a region of plastic failure 76 where the strain percentage increased at a relatively constant stress value prior to failure indicating a good degree of sample ductility. A second sample of PLLA 8.4 also generated a stress-strain curve 74 having a relatively greater region of plastic failure 78 also indicating a good degree of sample ductility.

Polymeric stents and other implantable devices made from such substrates may accordingly retain the material properties from the dip-coated polymer materials. The resulting stents, for instance, may exhibit mechanical properties which have a relatively high percentage ductility in radial, torsional, and/or axial directions. An example of this is a resulting stent having an ability to undergo a diameter reduction of anywhere between 5% to 70% when placed under an external load without any resulting plastic deformation. Such a stent may also exhibit high radial strength with, e.g., 0.1 N to 5 N per one cm length at 20% deformation. Such a stent may also be configured to self-expand when exposed to normal body temperatures.

The stent may also exhibit other characteristic mechanical properties which are consistent with a substrate formed as described herein, for instance, high ductility and high strength polymeric substrates. Such substrates (and processed stents) may exhibit additional characteristics such as a percent reduction in diameter of between 5% to 70% without fracture formation when placed under a compressive load as well as a percent reduction in axial length of between 10% to 50% without fracture formation when placed under an axial load. Because of the relatively high ductility, the substrate or stent may also be adapted to curve up to 180° about a 1 cm curvature radius without fracture formation or failure. Additionally, when deployed within a vessel, a stent may also be expanded, e.g., by an inflatable intravascular balloon, by up to 5% to 80% to regain diameter without fracture formation or failure.

These values are intended to illustrate examples of how a polymeric tubing substrate and a resulting stent may be configured to yield a device with certain mechanical properties. Moreover, depending upon the desired results, certain tubes and stents may be tailored for specific requirements of various anatomical locations within a patient body by altering the polymer and/or copolymer blends to adjust various properties such as strength, ductility, degradation rates, etc.

Figure 4B:
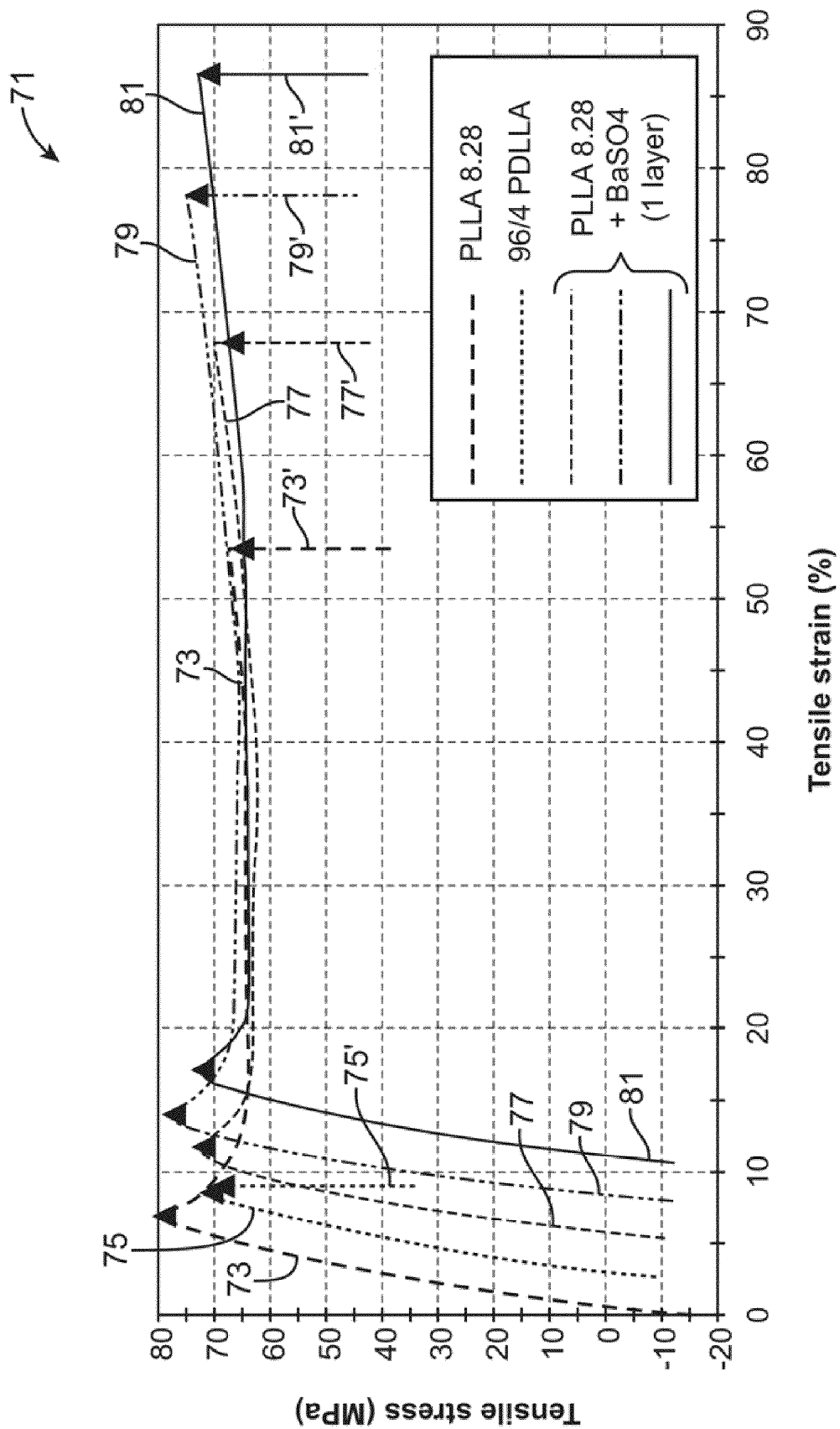
FIG. 4B illustrates another example of a stress-strain plot of additional samples formed by dip-coating along with samples incorporating a layer of $BaSO_4$.

FIG. 4B illustrates a plot 71 of additional results from stress-strain testing with additional polymers. A sample of PLLA 8.28 was formed utilizing the methods described herein and tested to generate stress-strain curve 73 having a point of failure 73'. Additional samples of PLLA 8.28 each with an additional layer of $BaSO_4$ for radiopacity incorporated into the tubular substrate were also formed and tested. A first sample of PLLA 8.28 with a layer of $BaSO_4$ generated stress-strain curve 77 having a point of failure 77'. A second sample of PLLA 8.28 also with a layer of $BaSO_4$ generated stress-strain curve 79 having a point of failure 79', which showed a greater tensile strain than the first sample with a slightly higher tensile stress level. A third sample of PLLA 8.28 with a layer of $BaSO_4$ generated stress-strain curve 81 having a point of failure 81', which was again greater than the tensile strain of the second sample, yet not significantly greater than the tensile stress level. The inclusion of $BaSO_4$ may accordingly improve the elastic modulus values of the polymeric substrates. The samples of PLLA 8.28 generally resulted in a load of between 100 N to 300 N at failure of the materials, which yielded elastic modulus values of between 1000 to 3000 MPa with a percent elongation of between 10% to 300% at failure.

A sample of 96/4 PDLLA was also formed and tested to generate stress-strain curve 75 having a point of failure 75' which exhibited a relatively lower percent elongation characteristic of brittle fracture. The resulting load at failure was between 100 N to 300 N with an elastic modulus of between 1000 to 3000 MPa, which was similar to the PLLA 8.28 samples. However, the percent elongation was between 10% to 40% at failure.

Figure 4C:
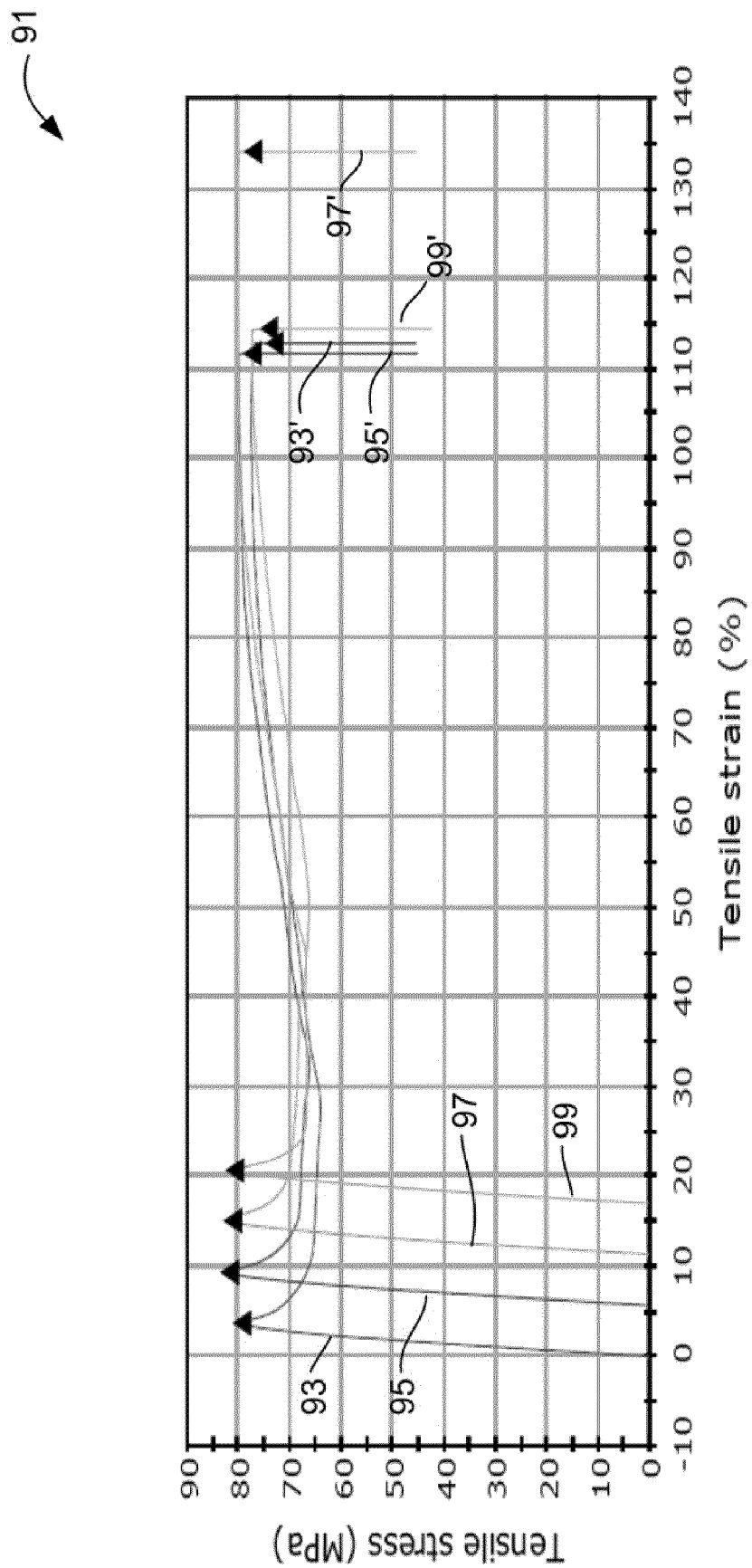
FIG. 4C illustrates yet another example of a stress-strain plot of additional samples which were formed with additional layers of PLLA.

In yet another experimental example of the ductility and retention of mechanical properties, PLLA with Iv 8.28 (high molecular weight) was obtained and tubular substrates were manufactured utilizing the dip-coating process described herein. The samples were formed to have a diameter of 5 mm with a wall thickness of 200 μm and were comprised of 8 layers of PLLA 8.28. The mandrel was immersed 8 times into the polymeric solution and the substrates were dried or cured in an oven to obtain a 25% to 35% crystalline structure. At least four samples of tubular substrates were subjected to tensile testing and the stress-strain plot 91 was generated from the stress-strain testing, as shown in FIG. 4C. The following Table 2 shows the resulting stress-strain parameters for the four samples, along with the average results (Avg.) and the deviation values (Dev.).

strate and to provide radiopacity. Additionally, the individual layers overlaid atop one another are fused to form a single cohesive layer rather than multiple separate layers as a result of the drying processes during the dipping process described herein. This results in a unitary structure which further prevents or inhibits any delamination from occurring between the individual layers.

Figure 5A:
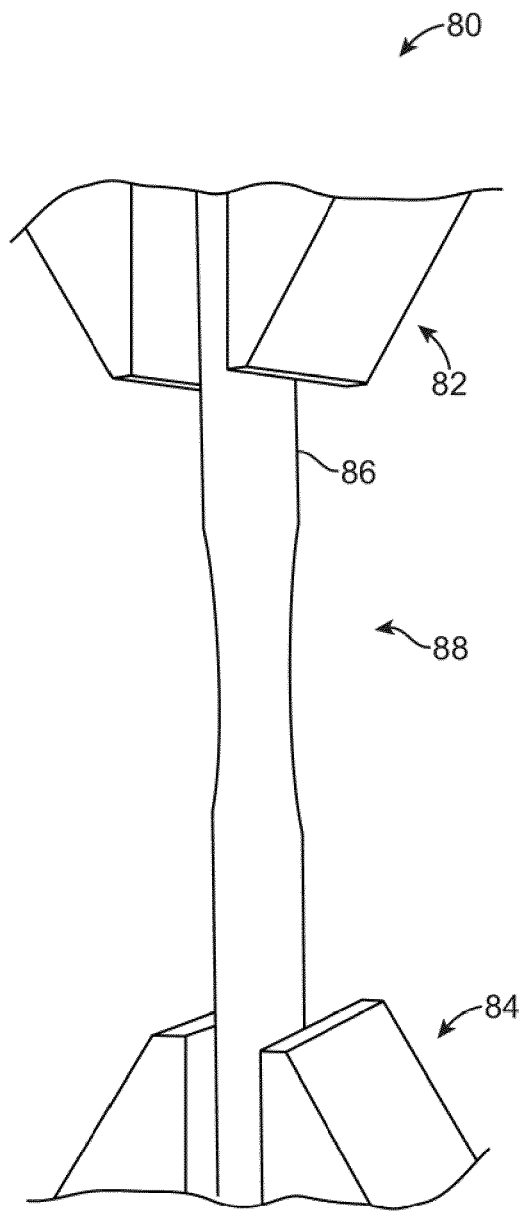
FIGS. 5A and 5B illustrate perspective views of an example of a dip-coat formed polymeric substrate undergoing plastic deformation and the resulting high percentage elongation.
Figure 5B:
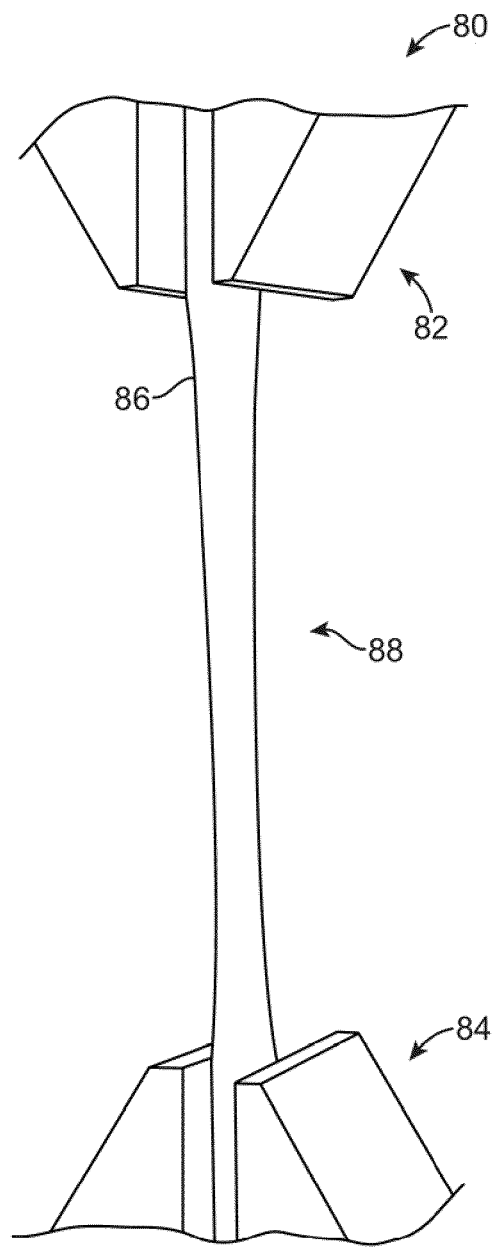

FIGS. 5A and 5B illustrate perspective views of one of the samples which was subjected to stress-strain testing on tensile testing system 80. The polymeric substrate specimen 86 was formed upon a mandrel, as described above, into a tubular configuration and secured to testing platform 82, 84. With testing platform 82, 84 applying tensile loading, substrate specimen 86 was pulled until failure. The relatively high percentage of elongation is illustrated by the stretched region of elongation 88 indicating a relatively high degree of plastic deformation when compared to an extruded polymeric substrate. Because a polymeric substrate formed via dip-coating as described above may be reduced in diameter via plastic deformation without failure, several different stent diameters can be manufactured from a single diameter substrate tube.

Dip-coating can be used to impart an orientation between layers (e.g., linear orientation by dipping; radial orientation by spinning the mandrel; etc.) to further enhance the mechanical properties of the formed substrate. As radial strength is a desirable attribute of stent design, post-processing of the formed substrate may be accomplished to impart such attributes. Typically, polymeric stents suffer from having relatively thick walls to compensate for the lack of radial strength, and this in turn reduces flexibility, impedes naviga-

TABLE 2

Stress-strain results of PLLA 8.28.

| No | OD (mm) | Wall thickness (mm) | Tensile stress at Yield (MPa) | Tensile strain at Yield (%) | Tensile load at break (MPa) | Tensile stress at break (MPa) | Tensile strain at break (%) | Modulus E (MPa) |
|---|---|---|---|---|---|---|---|---|
| 1 | 5.10 | 0.178 | 79.31 | 3.66 | 200.94 | 73.00 | 112.49 | 2696.00 |
| 2 | 5.09 | 0.175 | 81.70 | 3.61 | 208.84 | 77.29 | 105.71 | 2786.56 |
| 3 | 5.09 | 0.175 | 81.06 | 3.69 | 208.58 | 77.19 | 122.53 | 2692.60 |
| 4 | 5.10 | 0.177 | 80.62 | 3.73 | 202.93 | 74.09 | 97.21 | 2660.43 |
| Avg | 5.10 | 0.176 | 80.67 | 3.67 | 205.32 | 75.39 | 109.48 | 2708.90 |
| Dev | 0.01 | 0.002 | 1.01 | 0.05 | 4.00 | 2.18 | 10.71 | 54.20 |

The samples of PLLA 8.28 generally resulted in a percent elongation of between 97% to 123% at failure when placed under a 73 to 77 MPa stress load. As shown in the plot of FIG. 4C, a first sample (sample no. 1 of Table 2) of PLLA 8.28 generated a stress-strain curve 93 having a region of plastic failure 93' where the strain percentage increased at a relatively constant stress value prior to failure indicating a good degree of sample ductility. A second sample (sample no. 2 of Table 2) of PLLA 8.28 also generated a stress-strain curve 95 having a relatively smaller region of plastic failure 95' also indicating a good degree of sample ductility. Additional samples (sample nos. 3 and 4 of Table 2) having corresponding stress-strain curves 97, 99 and their corresponding regions of plastic failure 97', 99' are also shown.

Figure 4D:
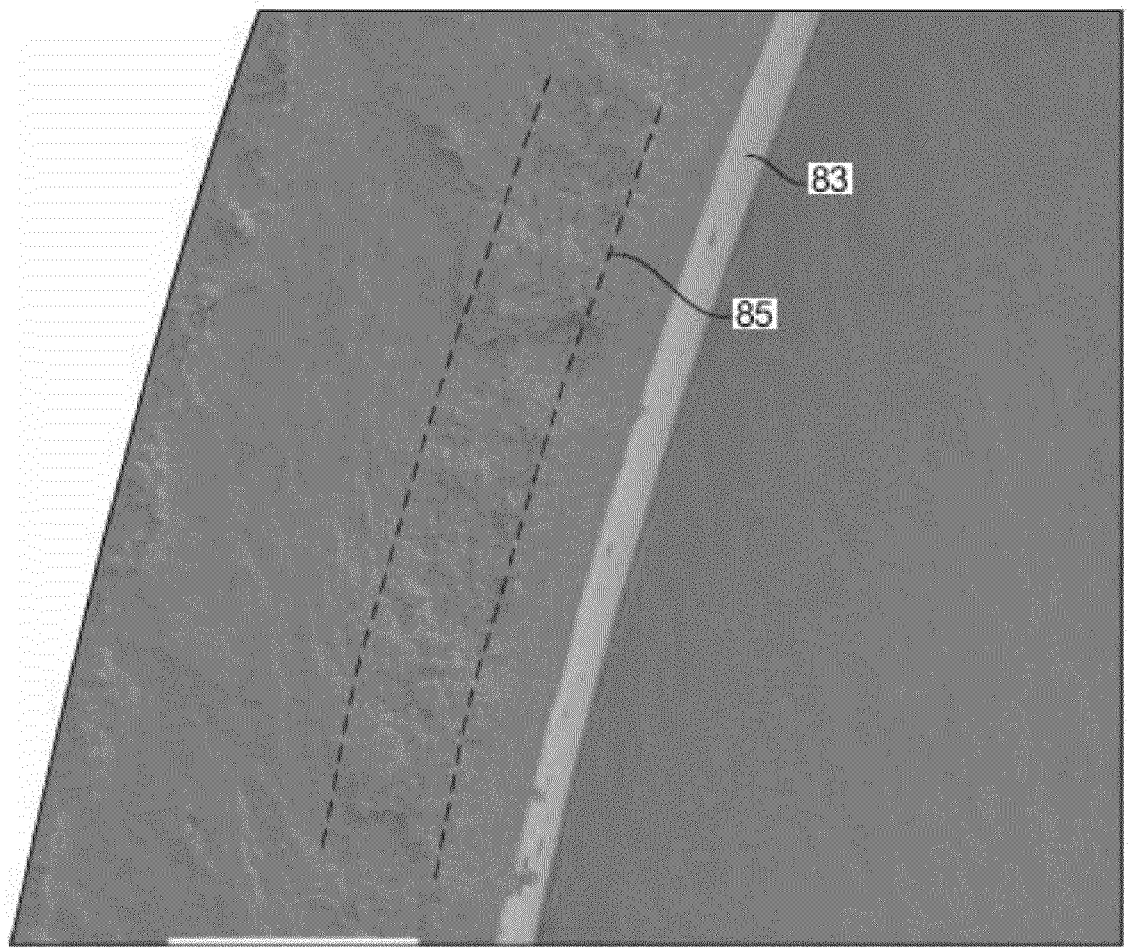
FIG. 4D illustrates an example of a detailed end view of a PLLA 8.28 substrate having a $BaSO_4$ layer incorporated into the substrate.

FIG. 4D illustrates an example of a detailed end view of a PLLA 8.28 substrate 83 formed with multiple dip-coated layers via a process described herein as viewed under a scanning electron microscope. This variation has a $BaSO_4$ layer 85 incorporated into the substrate. As described above, one or more layers of $BaSO_4$ may be optionally incorporated into substrate 83 to alter the elastic modulus of the formed subtion, and reduces arterial luminal area immediately post implantation. Post-processing may also help to prevent material creep and recoil (creep is a time-dependent permanent deformation that occurs to a specimen under stress, typically under elevated temperatures) which are problems typically associated with polymeric stents. By using a relatively high molecular weight in a range of, e.g., 259,000 g/mol to 2,120,000 g/mol, and controlling dipping parameters such as speed and temperature as well as the drying condition, the dipped substrates will have the following desirable properties: (1) high radial strength; (2) ductility; (3) malleability; and (4) isotropicity.

In further increasing the radial or circumferential strength of the polymeric substrate, a number of additional processes may be applied to the substrate after the dip-coating procedure is completed (or close to being completed). A polymer that is amorphous or that is partially amorphous will generally undergo a transition from a pliable, elastic state (at higher temperatures) to a brittle glass-like state (at lower temperature) as it transitions through a particular temperature, referred as the glass transition temperature ($T_g$). The glass transition temperature for a given polymer will vary, depending on the size and flexibility of side chains, as well as the flexibility of the backbone linkages and the size of functional groups incorporated into the polymer backbone. Below $T_g$, the polymer will maintain some flexibility, and may be deformed to a new shape. However, the further the temperature below $T_g$ the polymer is when being deformed, the greater the force needed to shape it.

Moreover, when a polymer is in glass transition temperature its molecular structure can be manipulated to form an orientation in a desired direction. Induced alignment of polymeric chains or orientation improves mechanical properties and behavior of the material. Molecular orientation is typically imparted by application of force while the polymer is in a pliable, elastic state. After sufficient orientation is induced, temperature of the polymer is reduced to prevent reversal and dissipation of the orientation.

In one example, the polymeric substrate may be heated to increase its temperature along its entire length or along a selected portion of the substrate to a temperature that is at or above the $T_g$ of the polymer. For instance, for a substrate fabricated from PLLA, the substrate may be heated to a temperature between 60° C. to 70° C. Once the substrate has reached a sufficient temperature such that enough of its molecules have been mobilized, a force may be applied from within the substrate or along a portion of the substrate to increase its diameter from a first diameter $D_1$ to a second increased diameter $D_2$ for a period of time necessary to set the increased diameter. During this setting period, the application of force induces a molecular orientation in a circumferential direction to align the molecular orientation of polymer chains to enhance its mechanical properties. The re-formed substrate may then be cooled to a lower temperature typically below $T_g$, for example, by passing the tube through a cold environment, typically dry air or an inert gas to maintain the shape at diameter $D_2$ and prevent dissipation of molecular orientation.

The force applied to the substrate may be generated by a number of different methods. One method is by utilizing an expandable pressure vessel placed within the substrate. Another method is by utilizing a braid structure, such as a braid made from a super-elastic or shape memory alloy like NiTi alloy, to increase in size and to apply the desirable degree of force against the interior surface of the substrate.

Figure 6:
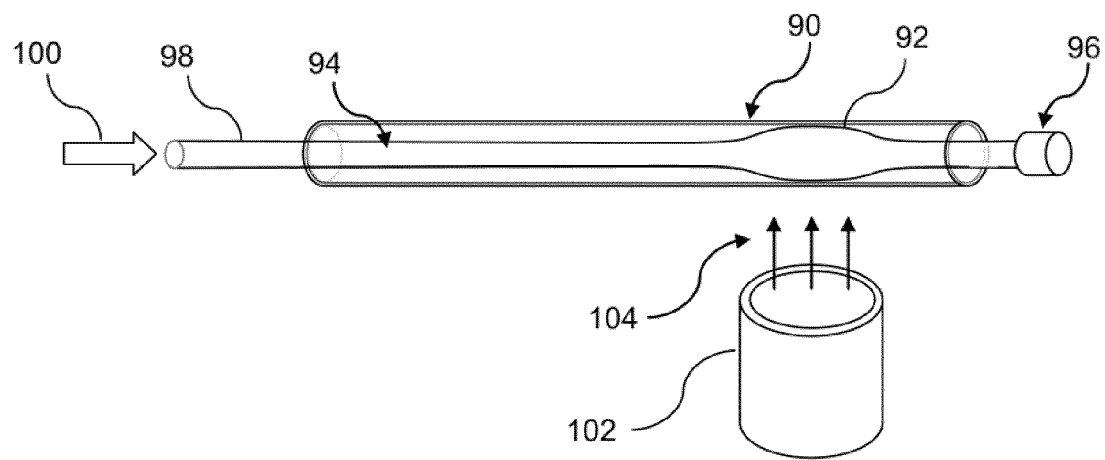
FIG. 6 illustrates an example of an additional forming procedure where a formed polymeric substrate may be expanded within a molding or forming tube to impart a circumferential orientation into the substrate.

Yet another method may apply the expansion force by application of a pressurized inert gas such as nitrogen within the substrate lumen, as shown in FIG. 6, to impart a circumferential orientation in the substrate. A completed substrate, e.g., cast cylinder 94, may be placed inside a molding tube 90 which has an inner diameter that is larger than the cast cylinder 94. Molding tube 90 may be fabricated from glass, highly-polished metal, or polymer. Moreover, molding tube 90 may be fabricated with tight tolerances to allow for precision sizing of cast cylinder 94.

A distal end or distal portion of cast cylinder 94 may be clamped 96 or otherwise closed and a pressure source may be coupled to a proximal end 98 of cast cylinder 94. The entire assembly may be positioned over a nozzle 102 which applies heat 104 to either the length of cast cylinder 94 or to a portion of cast cylinder 94. The pressurized inert gas 100, e.g., pressured to 10 to 400 psi, may be introduced within cast cylinder 94 to increase its diameter, e.g., 2 mm, to that of the inner diameter, e.g., 4 mm, of molding tube 90. The increase in diameter of cast cylinder 94 may thus realign the molecular orientation of cast cylinder 94 to increase its radial strength and to impart a circumferential orientation in the cast cylinder 94. Portion 92 illustrates radial expansion of the cast cylinder 94 against the inner surface of the molding tube 90 in an exaggerated manner to illustrate the radial expansion and impartation of circumferential strength. After the diameter has been increased, cast cylinder 94 may be cooled, as described above.

Once the substrate has been formed and reduced in diameter to its smaller second diameter, the stent may be processed, as described above. Alternatively, the stent may be processed from the substrate after initial formation. The stent itself may then be reduced in diameter to its second reduced diameter.

In either case, once the stent has been formed into its second reduced diameter, the stent may be delivered to a targeted location within a vessel of a patient. Delivery may be effected intravascularly utilizing known techniques with the stent in its second reduced delivery diameter positioned upon, e.g., an inflation balloon, for intravascular delivery. Once the inflation catheter and stent has been positioned adjacent to the targeted region of vessel, the stent may be initially expanded into contact against the interior surface of the vessel.

With the stent expanded into contact against the vessel wall at a third diameter which is larger than the second delivery diameter, the inflation balloon may be removed from the stent. Over a predetermined period of time and given the structural characteristics of the stent, the stent may then also self-expand further into contact against the vessel wall for secure placement and positioning.

Because thermoplastic polymers such as PLLA typically soften when heated, the cast cylinder 94 or a portion of the cast cylinder 94 may be heated in an inert environment, e.g., a nitrogen gas environment, to minimize its degradation.

Figure 7:
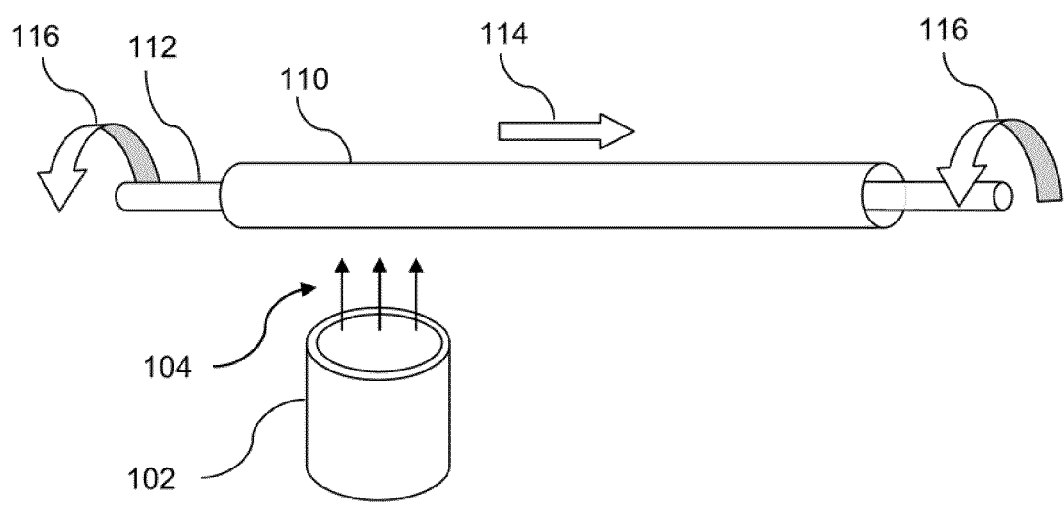
FIG. 7 illustrates another example of an additional forming procedure where a formed polymeric substrate may be rotated to induce a circumferentially-oriented stress value to increase the radial strength of the substrate.

Another method for post-processing a cast cylinder 110 may be seen in the example of FIG. 7 for inducing a circumferential orientation in the formed substrate. As illustrated, mandrel 112 having the cast cylinder 110 may be re-oriented into a horizontal position immediately post dip-coating before the polymer is cured. Mandrel 112 may be rotated, as indicated by rotational movement 116, at a predetermined speed, e.g., 1 to 300 rpm, while the cylinder 110 is heated via nozzle 102. Mandrel 112 may also be optionally rotated via motor 48 of assembly 30 to impart the rotational motion 54, as shown above in FIG. 2. Mandrel 112 may also be moved in a linear direction 114 to heat the length or a portion of the length of the cylinder 110. As above, this post-processing may be completed in an inert environment.

Figure 8:
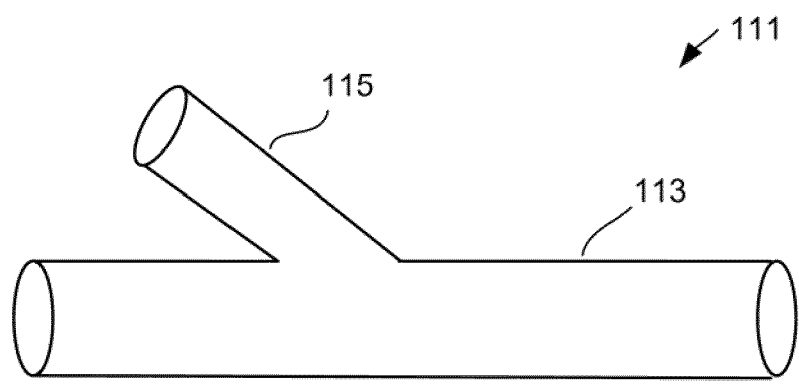
FIG. 8 illustrates a side view of a "y"-shaped mandrel which may be utilized to form a bifurcated stent via the dip coating process.

In other variations, the mandrel itself may be fabricated into alternative configurations aside from a cylindrical shape to impart these configurations directly into the substrates formed thereupon. An example is illustrated in the side view of FIG. 8 which shows a bifurcated "y"-shaped mandrel 111 comprised of an elongate primary support member 113 (having a circular, elliptical, or any other cross-sectional area, as desired) with a secondary branching support member 115 projecting at an angle from primary support member 113. The mandrel 111 may be fabricated as a single, integral piece or from several individual portions which may be assembled and de-assembled to assist in fabricating a substrate or removing a formed substrate from the mandrel 111. A multi-directional dipping process, such as three-dimensional dipping while rotating, as well as multi-directional curing, such as three-dimensional curing while rotating, may be utilized to form and maintain a uniform wall thickness of the substrate over the length of mandrel 111 to form an integral and uniform bifurcated substrate and subsequently a bifurcated stent scaffold.

Figure 9:
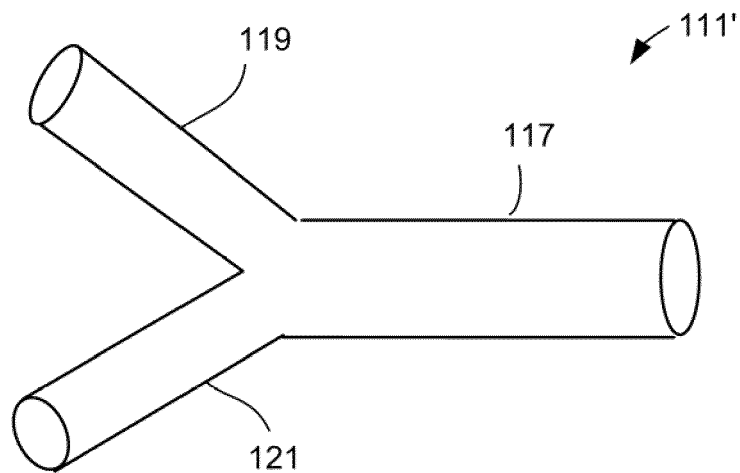
FIG. 9 illustrates a side view of another "Y"-shaped mandrel which may be utilized to form a bifurcated stent where each secondary branching member is angled with respect to one another.

Another variation is shown in the side view of FIG. 9 which shows a bifurcated "Y"-shaped mandrel 111' having an elongated primary support member 117 which branches in a bifurcation into at least two secondary branching support members 119, 121 which are angled with respect to each other as well as with respect to primary support member 117. Such a mandrel 111' may be formed of a singular integral piece or formed from individual portions which are attached to one another for forming the substrate and removing the substrate from the mandrel 111'.

Figure 10:
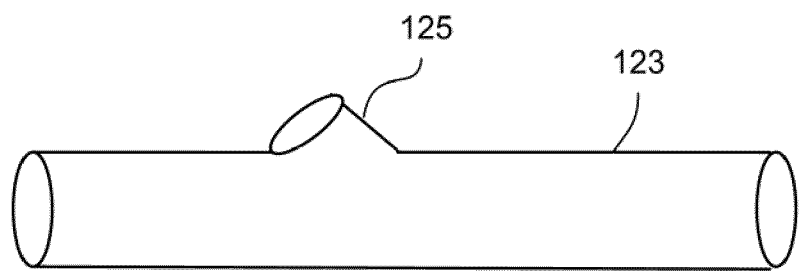
FIG. 10 illustrates a side view of yet another mandrel which defines a protrusion or projection for forming a stent having an angled access port.

Yet another variation is shown in the side view of FIG. 10, which shows a mandrel having a primary support member 123 with a protrusion 125 extending at an angle with respect to primary support member 123. Protrusion 125 may just extend beyond support member 123 to form a substrate and stent scaffold which has a portal formed about protrusion 125. A stent formed with such a portal may be commonly used for accessing a side branch vessel extending from a primary vessel.

Figure 11:
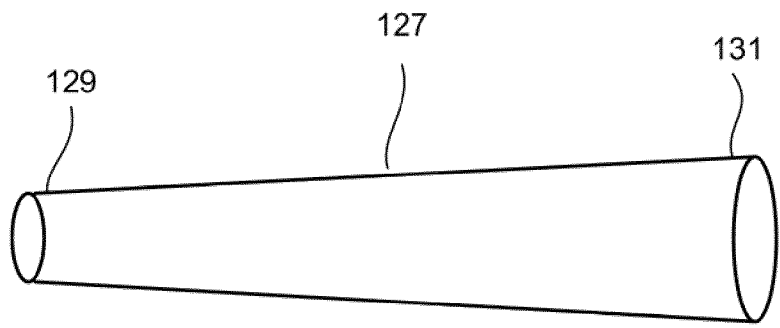
FIG. 11 illustrates a side view of yet another mandrel which may be used to form a stent which is tapered along its length.

In yet another variation as illustrated in FIG. 11 for directly forming substrates (and stent scaffolds) having alternative configurations, a tapered mandrel 127 having an elongate body which tapers from a narrowed end 129 to a widened end 131 may be utilized to subsequently form tapered stent prostheses which may be implanted along vessels which taper to prevent over-stretching of the vessel and minimize any injuries. The length and angle of tapering may be adjusted along the mandrel 127 to form a substrate which is suited for a particular anatomy, if so desired. Yet another variation includes dip coating a metallic stent (such as a stainless steel or Nitinol stent) into a polymeric solution as described herein where the solution incorporates one or more drugs or radiopaque agents such as Pt/Ir, gold, or tungsten, etc. The polymeric coating can be used to deliver or elute drugs or the coating may be used to enhance radiopacity of the stent while the coated stent is able to maintain radial forces via its metallic structure.

Figure 12:
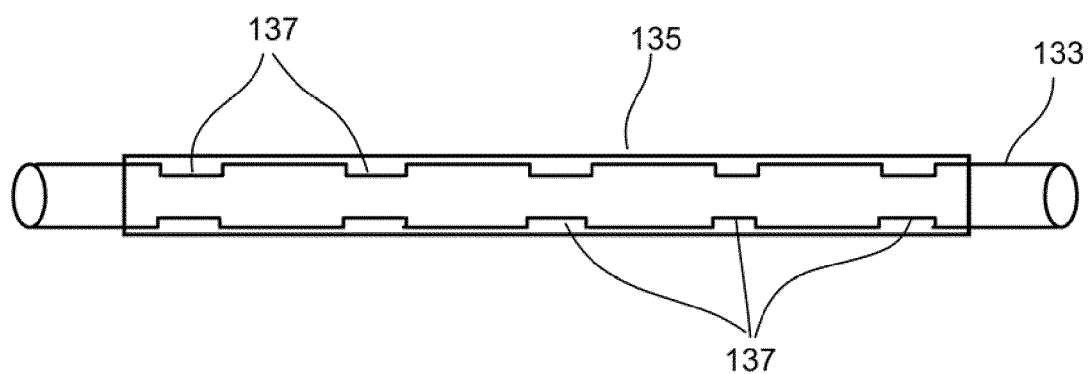
FIG. 12 illustrates a side view of yet another mandrel which defines depressions or features for forming a substrate having a variable wall thickness.

As discussed above, another method for substrate and stent fabrication is to form a substrate having a variable wall thickness, as illustrated in the side view of FIG. 12. In this variation, a dipping mandrel 133 having one or more diameters or surface features may be utilized. The variations in diameters or features may be produced by forming one or more depressions or features 137, e.g., peaks and valleys, along the surface of mandrel 133. These depressions or features 137 may be uniformly or arbitrarily located along the mandrel 133. The polymeric substrate 135 formed upon mandrel 133 utilizing the methods herein may thus be formed to have the corresponding features defined on the inner surface along its length. Thus, the resulting stent having a variable wall thickness structure may provide increased longitudinal flexibility while retaining other desirable stent qualities such as radial strength equal to or greater than existing endovascular stents.

The dipping process does not require a high temperature. The operation is typically conducted under ambient or below ambient temperatures. At such a temperature, pharmaceutical agents can be distributed into the polymer matrix without thermal effects, which tends to denature most drugs. The drug may also be protected from oxidization by an inert dipping environment and vacuum drying at a very low temperature Alternatively and as described above a surface of the mandrel can be formed in a pattern configured to form holes or voids (e.g., cylindrically or rectangularly shaped) into the inner layer of polymer substrate. The formed holes or voids may be formed, for instance, to have a volume of 10-100 μl. These structures may function as reservoirs and can be used to hold various materials for delivery into the patient (e.g., drug molecules, peptides, biological reagents, etc.) by dip coating a substrate into a reservoir containing the material to be introduced into the holds or voids where the solution has a relatively low viscosity ranging from $1.0 \times 10^{-3}$ to $50 \times 10^{-3}$ Pa·s. Filling of the holes or voids can also be accomplished by directly inject the eluting material into the holes or voids along the substrate. By doing so, the drugs, peptide, biological agents, etc. that are sensitive to temperature can be incorporated directly into the substrate and/or stent for release from the implanted prosthesis. In some variations, the implanted prosthesis can optionally include at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In other variations, optionally in combination with one or more other variations described herein, the implantable prosthesis can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), Biolimus A9 (Biosensors International, Singapore), AP23572 (Ariad Pharmaceuticals), prodrugs thereof, co-drugs thereof, and combinations thereof.

An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, firobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind, and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., J. Biomed. Mater. Res., 70A:10-19 (2004). Endothelial cells can be selectively targeted (for the targeted delivery of immunoliposomes) using scFv A5. T. Volkel, et al., Biochimica et Biophysica Acta, 1663:158-166 (2004). Junction membrane protein vascular endothelial (VE)-cadherin has been shown to bind to endothelial cells and down regulate apoptosis of the endothelial cells. R. Spagnuolo, et al., Blood, 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Tyr-Gly (SEQ ID NO: 1)). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the implantable device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, dexamethasone acetate, rapamycin, rapamycin derivatives, 40-O-(2-hydroxy)ethyl-rapamycin (everolimus), 40-O-(2-ethoxy)ethyl-rapamycin (bio limus), 40-O-(3-hydroxy) propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), Biolimus A9 (Biosensors International, Singapore), AP23572 (Ariad Pharmaceuticals), pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is everolimus. In another specific embodiment, the bioactive agent is clobetasol.

An alternative class of drugs would be p-para-agonists for increased lipid transportation, examples include feno fibrate.

In some embodiments, optionally in combination with one or more other embodiments described herein, the at least one biologically active agent specifically cannot be one or more of any of the bioactive drugs or agents described herein.

A prosthesis described above having one or more holes or voids can also be used to treat, prevent, or ameliorate any number of medical conditions located at the downstream vessel where the vessel is too narrow to allow any device to pass. By incorporation of the controlled release of various agents, these therapeutic agents may be delivered to the diseased area to provide for a regional therapy treatment carried out without the side effects that may be observed for a systematic treatment. Some exemplary treatments include delivering chemotherapeutical agents for tumor, anti inflammatory agents for kidney chronic glomerulonephritis, blood clot preventing agents for heart small vessel disease, small vessel arterial disease, small vessel peripheral arterial disease, and peripheral pulmonary vessel disease.

Figure 13:
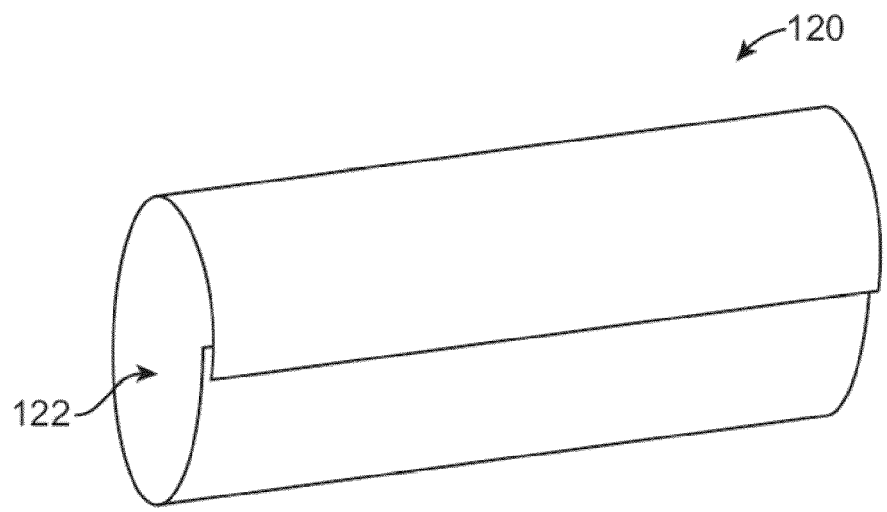
FIG. 13 illustrates a perspective view of one example of a rolled sheet stent which may be formed with the formed polymeric substrate.
Figure 14:
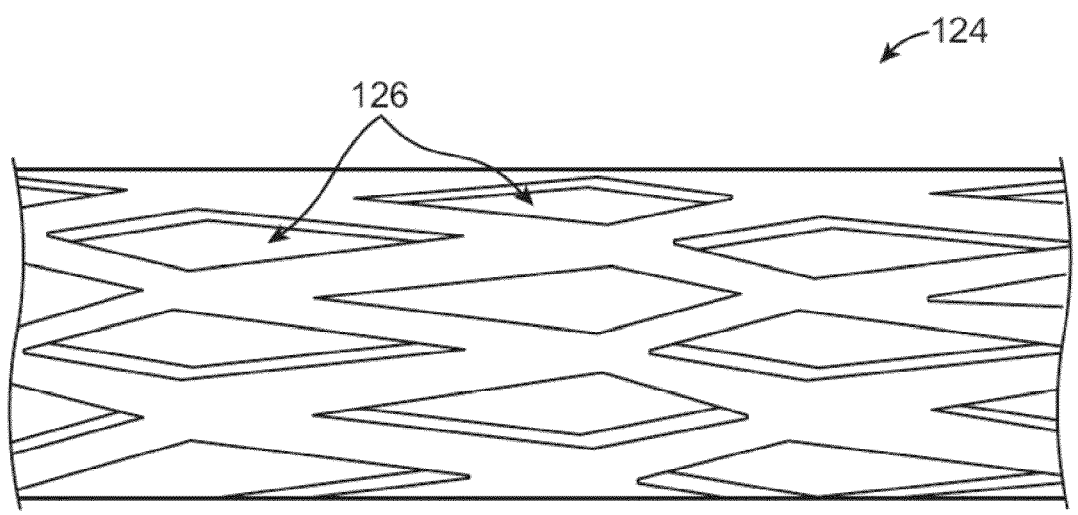
FIG. 14 illustrates a side view of another example of a stent machined via any number of processes from the resulting polymeric substrate.

Once the processing has been completed on the polymeric substrate, the substrate may be further formed or machined to create a variety of device. One example is shown in the perspective view of FIG. 13, which illustrates rolled stent 120. Stent 120 may be created from the cast cylinder by cutting along a length of the cylinder to create an overlapping portion 122. The stent 120 may then be rolled into a small configuration for deployment and then expanded within the patient vasculature. Another example is illustrated in the side view of stent 124, as shown in FIG. 14, which may be formed by machining a number of removed portions 126 to create a lattice or scaffold structure which facilitates the compression and expansion of stent 124 for delivery and deployment.

Aside from the design of stent 124 described above, other stent designs may be utilized which are particularly attuned to the physical and mechanical characteristics provided by the resulting polymeric substrate. Such stent designs may be mechanically optimized to take advantage of the ductility and strength characteristics provided by the polymeric material to result in a stent which is capable of experiencing between 10% to 80% material strain during the crimping process. For example, the starting diameter of a stent which is formed from a cured substrate may be initially at, e.g., 5 mm, and end with a crimped diameter of between, e.g., 2 to 2.8 mm. Further crimping to an even smaller diameter can increase the material strain above 100%.

Moreover, the optimized stent design may possess a relatively high fatigue life for a range of deformations by taking advantage of linear elastic properties possessed by the substrate prior to the initiation of any plastic deformation. The stent design may be modified based on physiologic conditions and materials selected so that when the stent is experiencing deformations caused by, e.g., physiologic conditions, the stent experiences material strain values that lie within the range of elastic deformation of the selected material.

Figure 15:
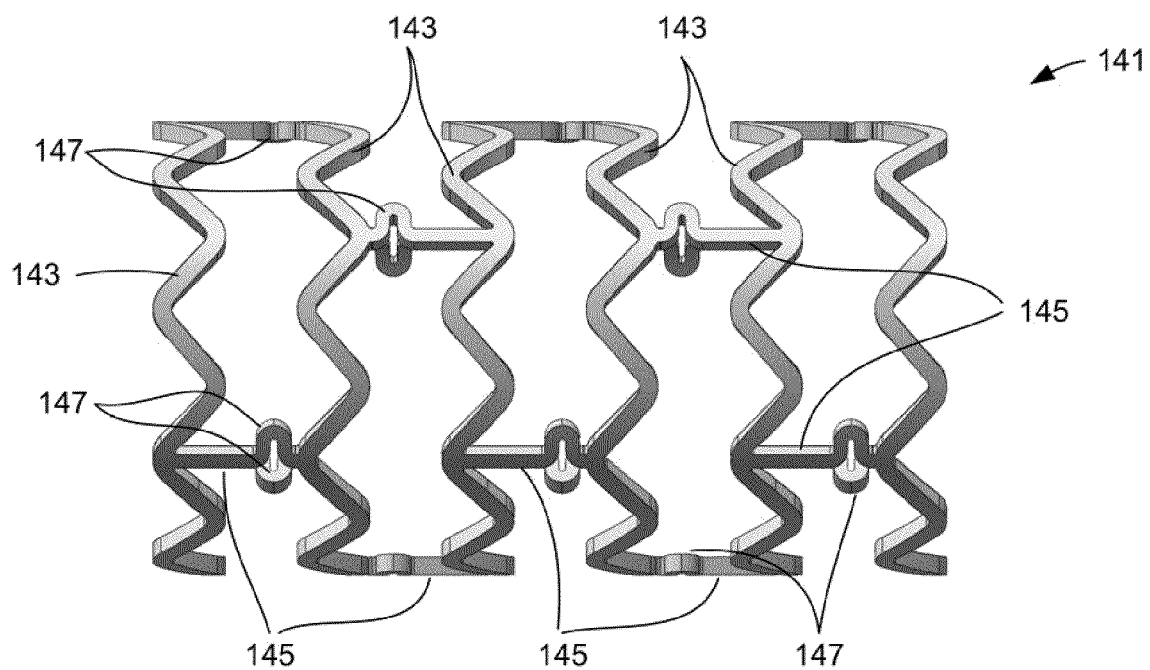
FIGS. 15 and 16 show examples of stent designs, respectively, which are optimized to take advantage of the inherent material properties of the formed polymeric substrate.
Figure 16:
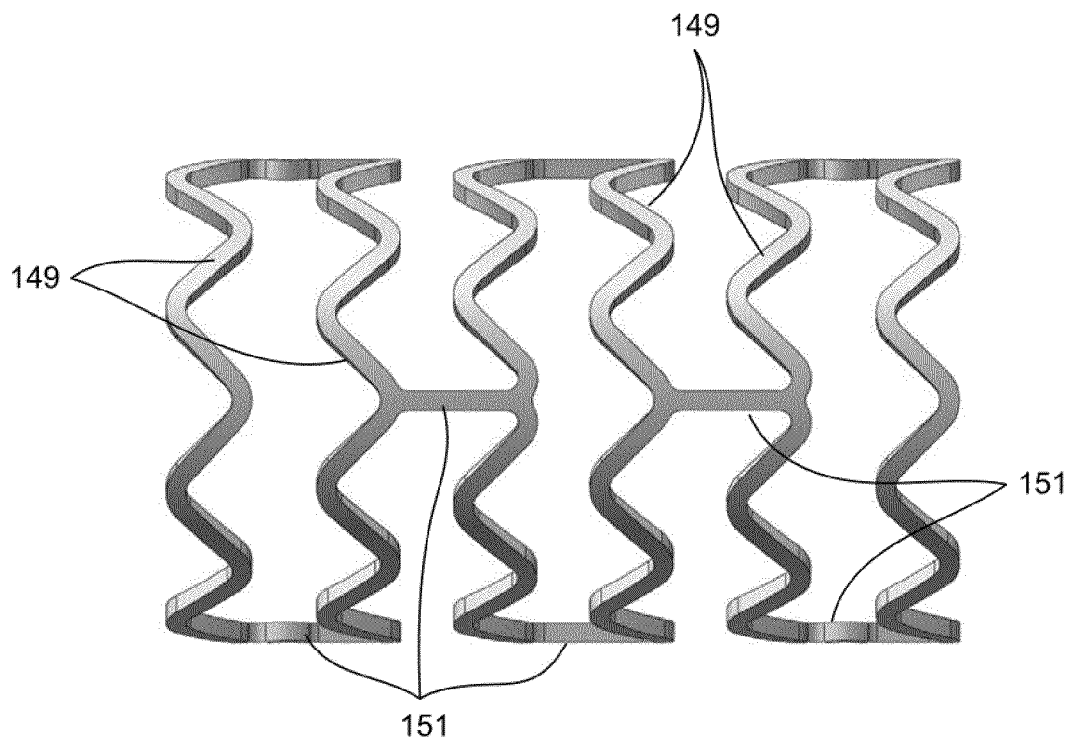

Examples of some optimized stent designs which take advantage of the inherent material properties of the formed polymeric substrate are illustrated in the side views of FIGS. 15 and 16. Such designs are particularly optimized for forming stents utilizing materials such as PLLA having the relatively high molecular weight described herein with a crystallinity of, e.g., 20%-40%. Such a stent may be utilized in a region of a patient's body which is subjected to high dynamic forces, such as the SFA, as discussed above. As discussed above, high molecular weight PLLA may have an elastic recoil ranging from, e.g., 0% to 4%, and stent designs as shown may typically experience physiologic conditions which induce material strain of less than 5% in axial, radial, and bending modes.

The stent designs may also accommodate relatively high levels of deformation in a variety of modes (radial, axial, bending, etc) while staying within, e.g., a 150% material strain limit, of various substrate materials. Examples of such high strain situations include crushing, shortening, stretching, and bending of the stent due to motion and external forces. The stent designs thus allow the stent to withstand such motion without fracturing by maintaining material strain below the ultimate strain of the material.

As shown in the side view of FIG. 15, stent 141 may include a number of undulating circumferential support element 143 which are coupled to one another via one or more linking or coupling elements 145. Although illustrated with six support elements 143, the number of support elements 143 may be varied depending upon the desired length of the overall stent 141 to be implanted. The support elements 143 may form an undulating wave which are coupled by one or more, e.g., three, linking or coupling elements 145, which are aligned in parallel and uniformly and circumferentially spaced apart relative to one another with respect to a longitudinal axis defined by the stent 141. The coupling elements 145 may incorporate or define a curved or arcuate section 147 along its length where the section 147 defines a radius which is smaller than a radius defined by the undulating portions of support elements 143. These curved or arcuate sections 147 may serve a stress-relief function in the event that the stent 141 has a longitudinal force imparted upon the stent 141.

Another variations is illustrated in the side view of FIG. 16, which similarly shows one or more undulating circumferential support element 149, e.g., six support elements 149, which are similarly connected by one or more linking or coupling elements 151. In this example, two linking or coupling elements 151 which are apposed to one another along a circumference of support element 149 may connect or attach adjacent support elements 149 to one another. Each adjacent support element 149 may be coupled via the linking or coupling elements 151 aligned in an alternating pattern to provide the overall stent with sufficient flexibility along its length.

Figure 17A:
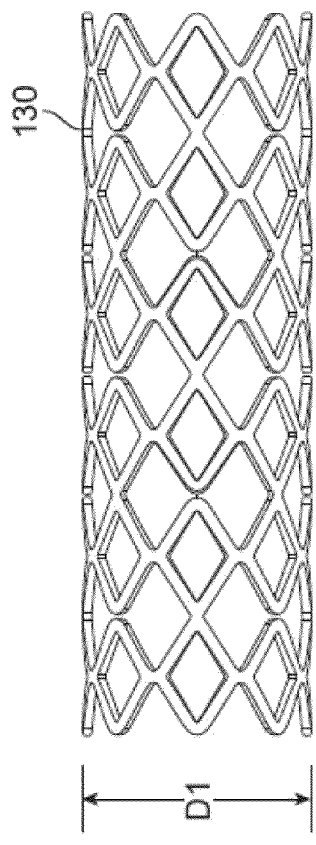
FIGS. 17A to 17F illustrate side views of another example of how a stent formed from a polymeric substrate may be delivered and deployed initially via balloon expansion within a vessel and then allowed to self-expand further in diameter to its initial heat set diameter.
Figure 17B:
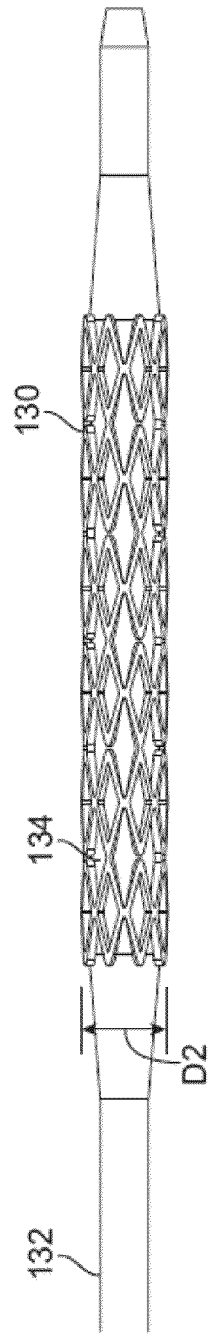

FIGS. 17A to 17F illustrate side views of another example of how a stent 130 formed from a polymeric substrate may be delivered and deployed for secure expansion within a vessel. FIG. 17A shows a side view of an exemplary stent 130 which has been processed or cut from a polymeric substrate formed with an initial diameter D1. As described above, the substrate may be heat treated at, near, or above the glass transition temperature $T_g$ of the substrate to set this initial diameter D1 and the substrate may then be processed to produce the stent 130 such that the stent 130 has a corresponding diameter D1. Stent 130 may then be reduced in diameter to a second delivery diameter D2 which is less than the initial diameter D1 such that the stent 130 may be positioned upon, e.g., an inflation balloon 134 of a delivery catheter 132, as shown in FIG. 17B. The stent 130 at its reduced diameter D2 may be self-constrained such that the stent 130 remains in its reduced diameter D2 without the need for an outer sheath, although a sheath may be optionally utilized. Additionally, because of the processing and the resultant material characteristics of the stent material, as described above, the stent 130 may be reduced from initial diameter D1 to delivery diameter D2 without cracking or material failure.

Figure 17C:
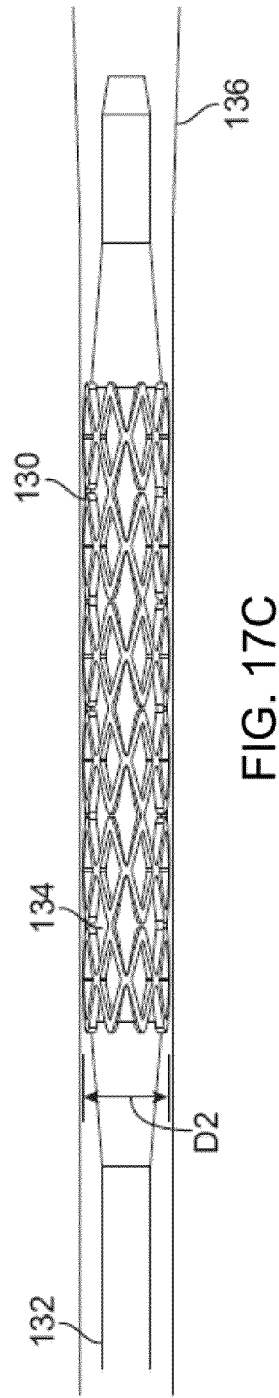
Figure 17D:
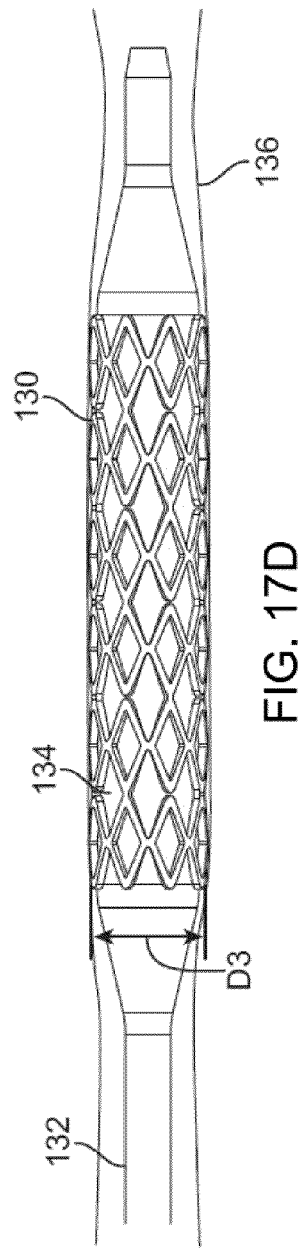
Figure 17E:
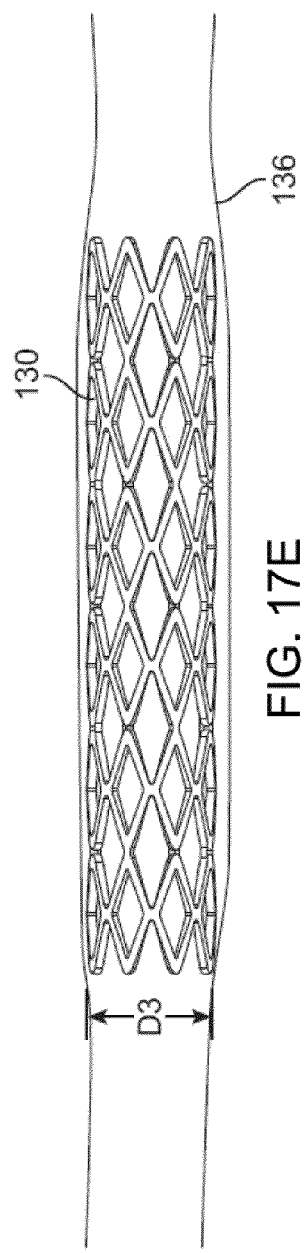

With stent 130 positioned upon delivery catheter 132, it may be advanced intravascularly within a vessel 136 until the delivery site is reached, as shown in FIG. 17C. Inflation balloon 134 may be inflated to expand a diameter of stent 130 into contact against the vessel interior, e.g., to an intermediate diameter D3, which is less than the stent's initial diameter D1 yet larger than the delivery diameter D2. Stent 130 may be expanded to this intermediate diameter D3, as shown in FIG. 17D, without any cracking or failure because of the inherent material characteristics described above. Moreover, expansion to intermediate diameter D3 may allow for the stent 130 to securely contact the vessel wall while allowing for the withdrawal of the delivery catheter 132, as shown in FIG. 17E.

Figure 17F:
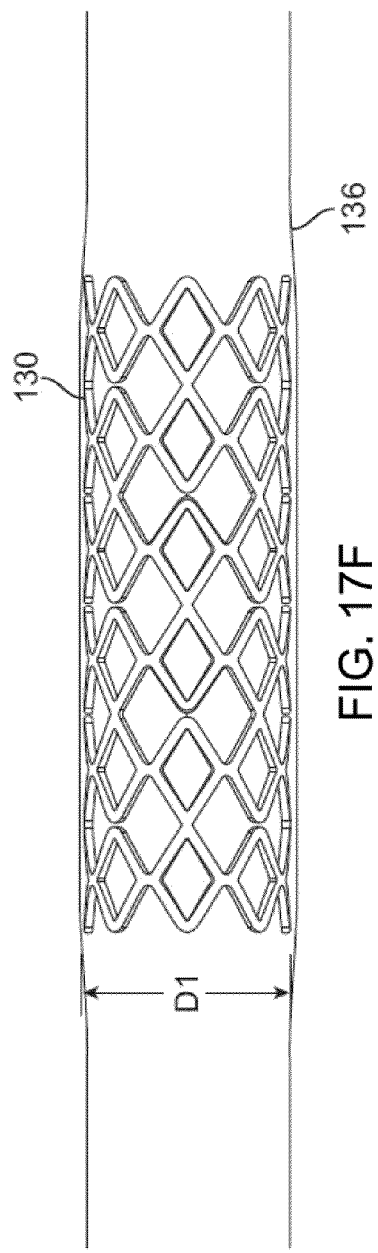

Once the stent 130 has been expanded to some intermediate diameter D3 and secured against the vessel wall, stent 130 may be allowed to then self-expand further over a period of time into further contact with the vessel wall such that stent 130 conforms securely to the tissue. This self-expansion feature ultimately allows for the stent 130 to expand back to its initial diameter D1 which had been heat set, as shown in FIG. 17F, or until stent 130 has fully self-expanded within the confines of the vessel diameter.

These examples are presented to be illustrative of the types of devices which may be formed and various other devices which may be formed from the polymeric substrate are also included within this disclosure.

The applications of the disclosed invention discussed above are not limited to certain processes, treatments, or placement in certain regions of the body, but may include any number of other processes, treatments, and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method of forming a polymeric substrate, comprising:
    immersing a mandrel into at least a first polymeric solution such that at least a first layer of a biocompatible polymer substrate is formed upon the mandrel and has a first diameter defined by the mandrel;
    curing the substrate;
    subjecting the substrate to a first elevated temperature at or above a glass transition temperature of the substrate;
    cooling the substrate in a controlled manner to a second temperature lower than the glass transition temperature such that the substrate transitions to a glass state and imparts a shape memory effect;
    forming an expandable stent scaffold having the first diameter;
    reducing the first diameter of the stent to a second smaller diameter, and
    wherein the stent experiences physiological condition-induced material strain less than 6% in axial, radial, and bending modes when placed within a vessel lumen in an expanded configuration.

2. The method of claim 1 wherein prior to reducing the first diameter, further comprising:
    controlling a number of immersions of the mandrel into the first polymeric solution;
    controlling a duration of time of each immersion of the mandrel; and
    controlling a delay time between each immersion of the mandrel.

3. The method of claim 2 further comprising controlling a withdrawal rate of the mandrel from the first polymeric solution after each immersion.

4. The method of claim 1 wherein the first polymeric solution comprises a polymer having a molecular weight ranging from 259,000 g/mol to 2,120,000 g/mol.

5. The method of claim 1 wherein a molecular weight of the first layer is configured to accelerate a degradation rate of the second layer.

6. The method of claim 1 wherein the first polymeric solution is selected from the group consisting of polyethylene, polycarbonates, polyamides, polyesteramides, polyetheretherketone, polyacetals, polyketals, polyurethane, polyolefin, polyethylene terephthalate, polylactide, poly-L-lactide, polyglycolide, poly(lactide-co -glycolide), polycaprolactone, caprolactones, polydioxanones, polyanhydrides, polyorthocarbonates, polyphosphazenes, chitin, chitosan, poly(amino acids), polyorthoesters, oligomers, homopolymers, methyl cerylate, methyl methacrylate, acryli acid, methacrylic acid, acrylamide, hydroxyethy acrylate, hydroxyethyl methacrylate, glyceryl scrylate, glyceryl methacrylate, methacrylamide, ethacrylamide, styrene, vinyl chloride, binaly pyrrolidone, polyvinyl alcohol, polycoprolactam, polylauryl lactam, polyjexamethylene adipamide, polyexamethylene dodecanediamide, trimethylene carbonate, poly(β-hydroxybutyrate), poly(g-ethyl glutamate), poly(DTH iminocarbonate), poly(bisphenol A iminocarbonate), polycyanoacrylate, polyphosphazene, methyl cerylate, methyl methacrylate, acryli acid, methacrylic acid, acrylamide, hydroxyethy acrylate, hydroxyethyl methacrylate, glyceryl scrylate, glyceryl methacrylate, methacrylamide, ethacrylamide, and copolymers, terpolymers and combinations and mixtures thereof.

7. The method of claim 1 wherein immersing a mandrel comprises further immersing the mandrel into a second polymeric solution such that a second layer of polymer is formed upon the first layer.

8. The method of claim 7 wherein a molecular weight of the first layer is configured to accelerate a degradation rate of the second layer.

9. The method of claim 7 wherein the second polymeric solution comprises a drug or agent selected from the group consisting of antipoliferative, antineoplastic, antigenic, anti-inflammatory, antirestenotic, antilipid, antimitotics, metalloproteinase inhibators, and anti-sclerosing agents.

10. The method of claim 7 wherein the second polymeric solution comprises a radio-opaque material.

11. The method of claim 7 wherein the second polymeric solution comprises a $BaSO_4$ solution.

12. The method of claim 2 wherein controlling a number of immersions comprises immersing the mandrel between 2 and 20 times.

13. The method of claim 2 wherein controlling a duration of time comprises immersing the mandrel between 15 seconds and 240 minutes.

14. The method of claim 2 wherein controlling a delay time comprises delaying immersion of the mandrel between 15 seconds and 60 minutes.

15. The method of claim 1 wherein immersing a mandrel comprises inserting the mandrel into the first polymeric solution at a rate of 5 mm/min to 1000 mm/min.

16. The method of claim 1 further comprising applying a force within a lumen defined through the polymeric substrate such that the substrate expands from a first diameter to a second larger diameter.

17. The method of claim 16 further comprising applying heat to the polymeric substrate while applying the force.

18. The method of claim 1 further comprising rotating the mandrel while applying heat.

19. The method of claim 1 further comprising controlling an angle of the mandrel relative to the polymeric solution.

20. The method of claim 1 wherein the substrate has a length of 1 cm to 40 cm.

21. The method of claim 1 further comprising controlling a relative humidity of less than 30%.

22. The method of claim 1 further comprising controlling a temperature of the polymeric solution to be below a boiling point of a solvent contained within the polymeric solution.

23. The method of claim 1 further comprising mold-transferring one or more patterns from an outer surface of the mandrel to an inner surface of the substrate.

24. The method of claim 1 further comprising controlling a crystallinity percentage of the substrate within a range of 10% to 50%.

25. The method of claim 1 wherein the substrate formed upon the mandrel is isotropic.

26. The method of claim 1 further comprising drying the substrate at a glass transition temperature of the polymeric solution.

27. The method of claim 1 further comprising:
    subjecting the substrate to a first elevated temperature above a glass transition temperature of the substrate while reducing the first diameter; and
    cooling the substrate to a second temperature lower than the glass transition temperature such that the substrate transitions to a glass state and imparts a shape memory effect.

28. The method of claim 27 wherein reducing comprises reducing the first diameter ranging from 3 mm to 10 mm to the second diameter ranging from 1.5 mm to 5 mm.

29. The method of claim 27 wherein cooling comprises reducing the substrate temperature to the second temperature below the glass transition temperature.

30. The method of claim 1 wherein the substrate formed upon the mandrel exhibits a 20% radial deformation when placed under a 0.1 N to 5 N per cm load.

31. The method of claim 1 wherein the substrate formed upon the mandrel exhibits a percent elongation of between 97% to 123% at failure when placed under the 73 to 77 MPa load.

32. The method of claim 1 wherein the substrate formed upon the mandrel exhibits a percent reduction in diameter of between 5% to 80% without fracture formation when placed under a compressive load.

33. The method of claim 1 further comprising expanding a diameter of the stent via an expandable balloon by 5% to 80% without fracture formation.

34. The method of claim 1 wherein the stent is adapted to exhibit a percent reduction in axial length of between 10% to 50% without fracture formation when placed under an axial load.

35. The method of claim 1 wherein immersing a mandrel comprises immersing the mandrel into the first polymeric solution having an inherent viscosity of about 4.3 to about 8.4 dl/g.

36. The method of claim 1 wherein curing the substrate comprises curing the substrate such that the substrate remains in a semi-crystalline state at or below an ambient temperature.

37. The method of claim 1 wherein cooling the substrate comprises actively cooling the substrate to the second temperature lower than the glass transition temperature.

* * * * *

UNITED STATES PATENT AND TRADEMARK OFFICE
CERTIFICATE OF CORRECTION

PATENT NO.      : 8,206,636 B2
APPLICATION NO. : 12/488453
DATED           : June 26, 2012
INVENTOR(S)     : Kamal Ramzipoor et al.

It is certified that error appears in the above-identified patent and that said Letters Patent is hereby corrected as shown below:

In column 7, line 58, please replace "50 to 10°C°" with --5° to 10°C--.

In column 21, line 57, please replace "temperature" with --temperature.--.

In column 27, line 28, please replace "variations" with --variation--.

Signed and Sealed this
Sixteenth Day of October, 2012

David J. Kappos
*Director of the United States Patent and Trademark Office*

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide

<400> SEQUENCE: 1

Asp Val Asp Val Pro Asp Gly Asp Ser Leu Ala Tyr Gly
1               5                   10
```